(12) United States Patent
Prygoski et al.

(10) Patent No.: US 11,185,353 B2
(45) Date of Patent: Nov. 30, 2021

(54) ANCHORS FOR VERTEBRAL BODY

(71) Applicant: OrthorPediatrics Corp., Warsaw, IN (US)

(72) Inventors: Matt Prygoski, Warsaw, IN (US); Evangelos Tozakoglou, Forty Wayne, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 0 days.

(21) Appl. No.: 16/361,967

(22) Filed: Mar. 22, 2019

(65) Prior Publication Data

US 2019/0290334 A1    Sep. 26, 2019

Related U.S. Application Data

(60) Provisional application No. 62/646,600, filed on Mar. 22, 2018.

(51) Int. Cl.
*A61B 17/70*    (2006.01)
*A61B 17/68*    (2006.01)
*A61B 17/56*    (2006.01)

(52) U.S. Cl.
CPC ...... *A61B 17/7053* (2013.01); *A61B 17/7022* (2013.01); *A61B 2017/564* (2013.01); *A61B 2017/681* (2013.01)

(58) Field of Classification Search
CPC .............. A61B 17/701; A61B 17/7053; A61B 17/7022; A61B 17/7049
See application file for complete search history.

(56) References Cited

U.S. PATENT DOCUMENTS

| | | | |
|---|---|---|---|
| 6,045,573 A | 4/2000 | Wenstrom, Jr. et al. | |
| 6,149,563 A | 11/2000 | Kusters | |
| 6,436,099 B1 | 8/2002 | Drewry et al. | |
| 6,517,542 B1 | 2/2003 | Papay et al. | |
| 7,285,121 B2 | 10/2007 | Braun et al. | |
| 7,658,751 B2 | 2/2010 | Stone et al. | |
| 7,727,259 B2 * | 6/2010 | Park .................. | A61B 17/7052 606/255 |
| 8,029,536 B2 | 10/2011 | Sorensen et al. | |
| 8,231,654 B2 | 7/2012 | Kaiser et al. | |
| 9,078,644 B2 | 7/2015 | Stone | |
| 9,271,713 B2 | 3/2016 | Denham et al. | |
| 9,642,661 B2 | 5/2017 | Stone et al. | |
| 2001/0037131 A1 | 11/2001 | Schmieding et al. | |
| 2005/0038428 A1 | 2/2005 | Kelman et al. | |
| 2007/0073293 A1 | 3/2007 | Martz et al. | |

(Continued)

FOREIGN PATENT DOCUMENTS

EP    1749504    2/2007

*Primary Examiner* — Jan Christopher L Merene
(74) *Attorney, Agent, or Firm* — John V. Daniluck; Gerald W. Roberts; Dentons Bingham Greenebaum LLP

(57) ABSTRACT

Implantable devices for dynamic interconnection between bones, and especially between vertebrae. Some devices include tethering heads that are independent of the bone connecting member (fastener, plate, hook, loop). The devices provide for various types of manipulation of a flexible connection such as a tether, such as by providing an aperture through which the flexible connection is passed and guided, or a post to which a loop of the flexible connection can be attached, or a groove in which a loop of the flexible connection can be placed.

13 Claims, 23 Drawing Sheets

(56) References Cited

U.S. PATENT DOCUMENTS

| | | |
|---|---|---|
| 2007/0112352 A1 | 5/2007 | Sorensen |
| 2007/0225708 A1* | 9/2007 | Biedermann ...... A61B 17/7037 606/279 |
| 2008/0058818 A1* | 3/2008 | Schwab ............. A61B 17/7032 606/328 |
| 2008/0300599 A1 | 12/2008 | Anapliotis et al. |
| 2009/0264933 A1* | 10/2009 | Carls .................. A61B 17/7032 606/264 |
| 2010/0160968 A1 | 6/2010 | Joshi et al. |
| 2011/0319945 A1 | 12/2011 | Tepic |
| 2012/0035671 A1 | 2/2012 | Hodge et al. |
| 2012/0109111 A1 | 5/2012 | Li |
| 2017/0007299 A1 | 1/2017 | Mundis, Jr. et al. |

\* cited by examiner

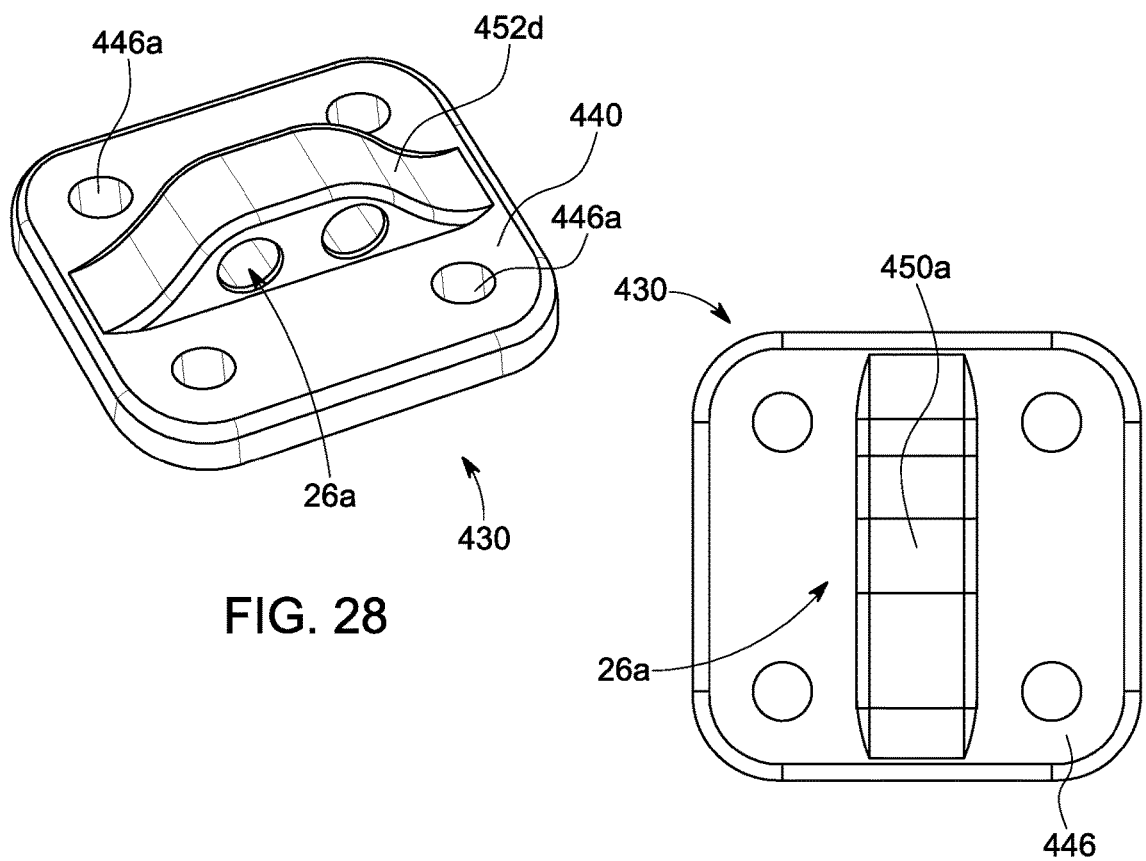
FIG. 28
FIG. 31
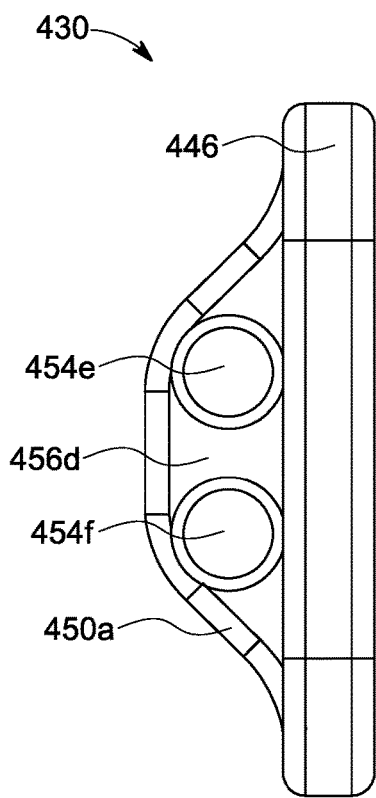
FIG. 29
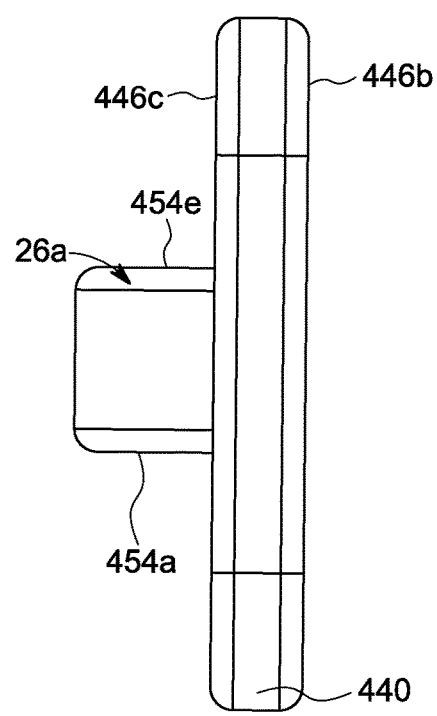
FIG. 30

Option 1: Simple Two Level Constructs

Option 3: Multiple Level Constructs, Single Loop Tensioned Across End Points

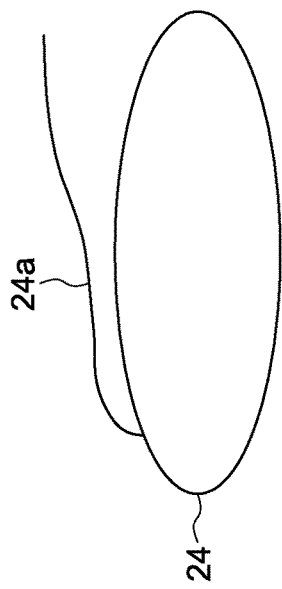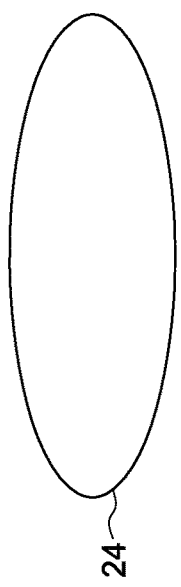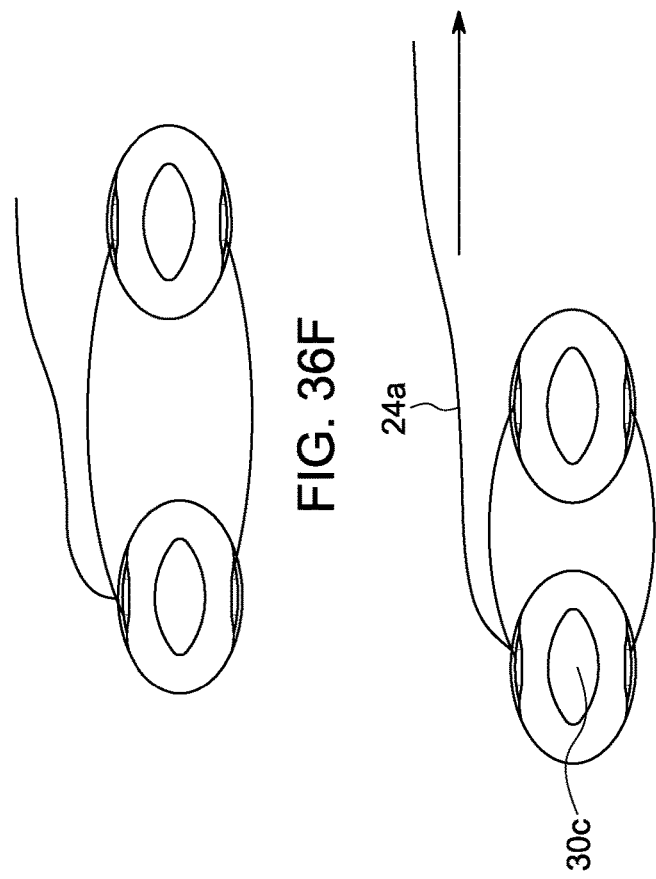
FIG. 36B
FIG. 36C
FIG. 36D
FIG. 36E
FIG. 36F
FIG. 36G Option 2: Multiple Level Constructs, Each Loop Tensioned Independently Option 4: Multiple Anchors for Derotation

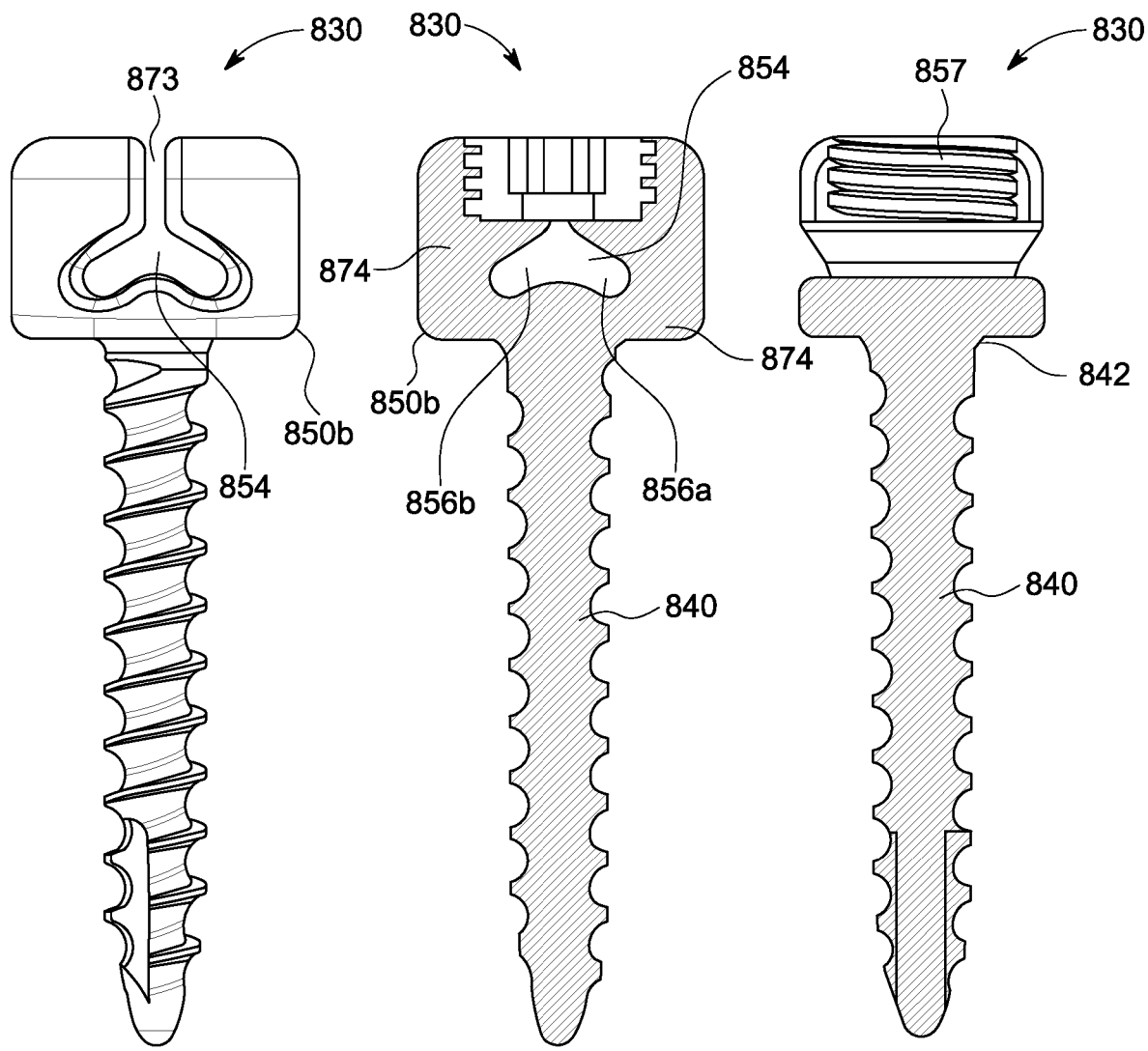
FIG. 42  FIG. 43  FIG. 44
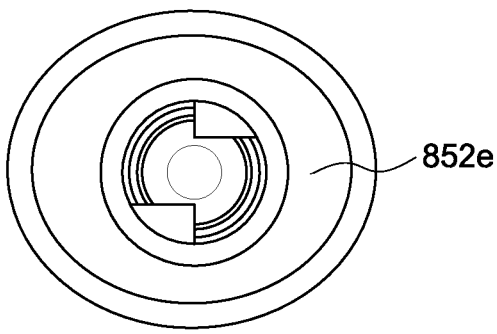
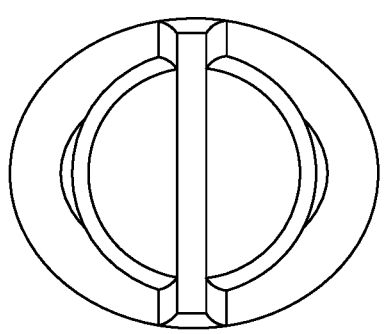
FIG. 45  FIG. 46

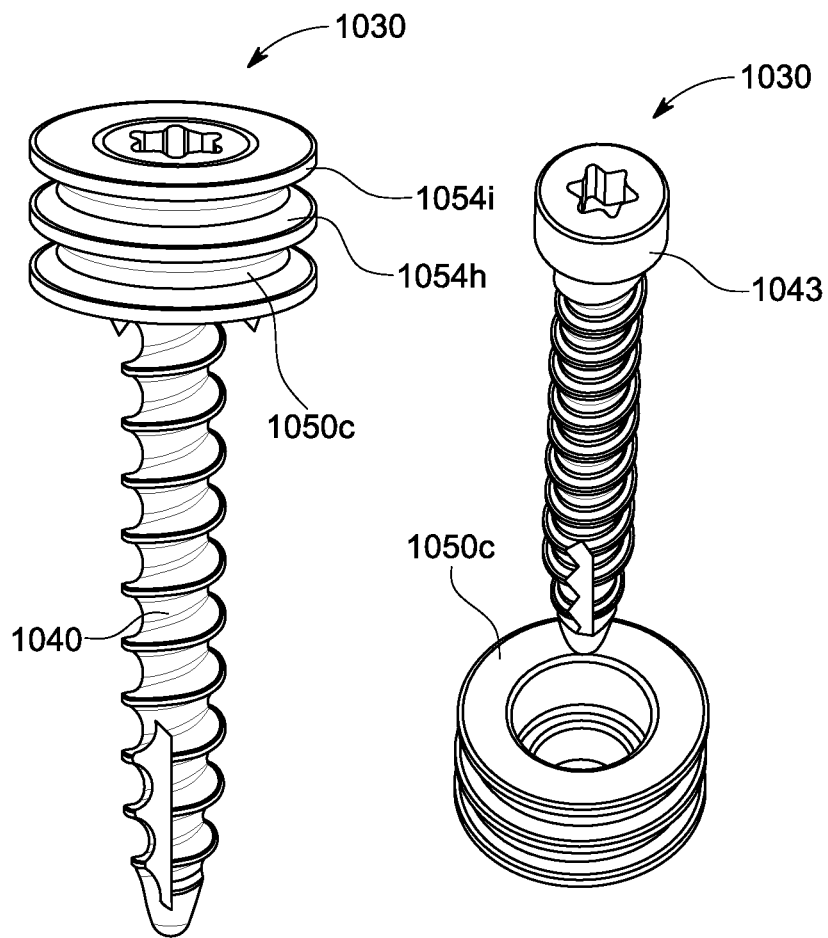
FIG. 56      FIG. 57
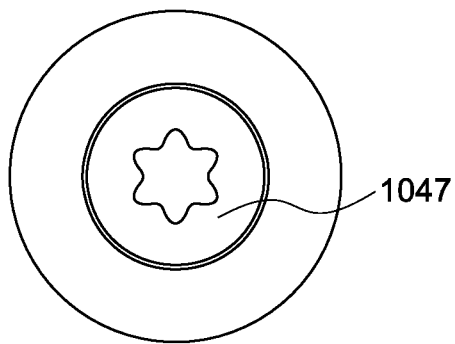
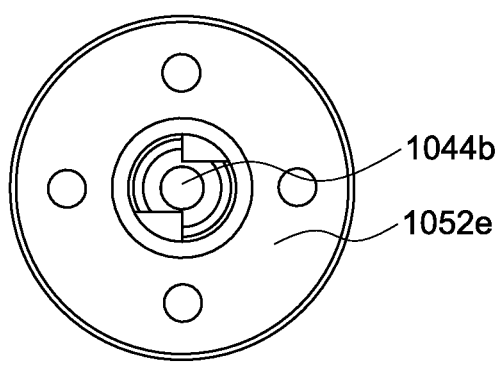
FIG. 58      FIG. 59

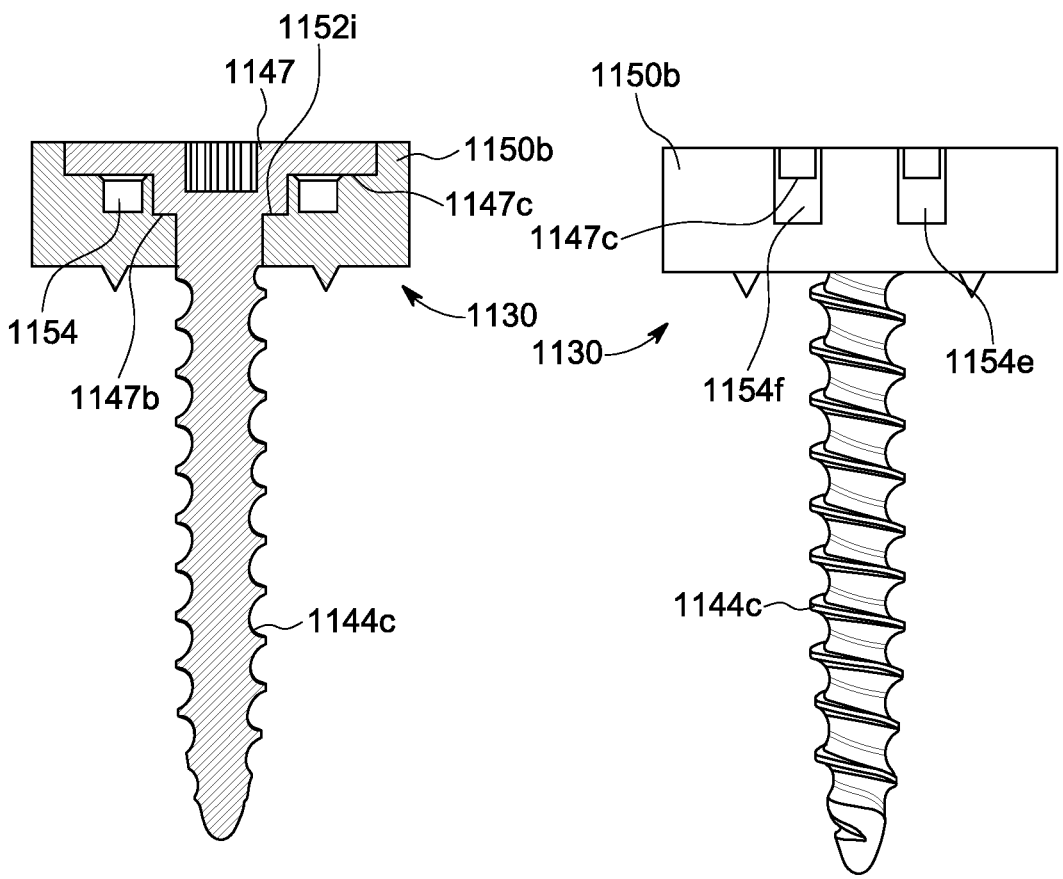
FIG. 65
FIG. 66
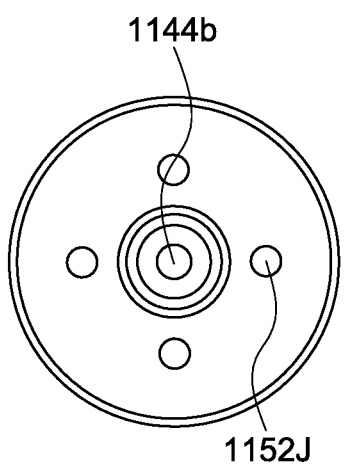
FIG. 67
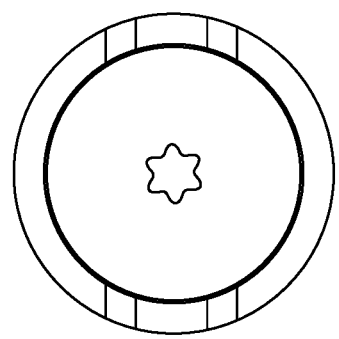
FIG. 68
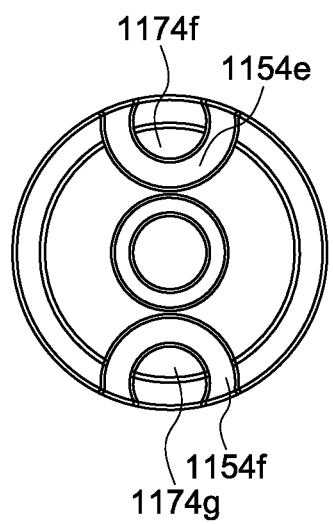
FIG. 69

ANCHORS FOR VERTEBRAL BODY

CROSS REFERENCE TO RELATED APPLICATION

This application claims the benefit of priority to U.S. Provisional Patent Application Ser. No. 62/646,600, filed Mar. 22, 2018, incorporated herein by reference.

FIELD OF THE INVENTION

Various embodiments of the present invention pertain to apparatus and methods for securing two objects by a flexible connection, and in other embodiments the interconnection of two vertebrae or other bones with a flexible connection, such as a tether or sutures.

BACKGROUND OF THE INVENTION

Vertebral body tethering (VBT) remains a procedure in the experimental phase. The behavior of long bone physes are well known and the effects of guided growth fairly predictable. This is not the case with the spine. Each vertebra has 2 end plates, acting as growth plates. How they respond to guided growth is not yet predictable. Previous work by Betz with the Nitinol staple and other authors shed some light on the topic. However, questions such as amount of tension, segmental differences in tension (and alteration over time under load) and the long term effects on the discs remain unanswered.

SUMMARY OF THE INVENTION

One aspect of the present invention pertains to a member for connection to a vertebra. Some embodiments include a head. Other embodiments include means for connecting the head to a vertebra. Still further embodiments include means for coupling the head to a flexible material.

Examples of flexible materials include suture and tethers fabricated from organic materials, and metallic wires. In some embodiments, the flexible material provides a non-rigid connection between two different members, with the flexible material capable of sustaining tension between the members, but substantially not capable of sustaining compression between the members. Tethers of any cross-sectional shape are contemplated, including substantially circular cross sections, elongate cross sections, square cross sections, and flat cross sections.

One aspect of the present invention pertains to a member for connection to a vertebra. Some embodiments include a head. Other embodiments include means for connecting the head to a vertebra and means for coupling the head to a flexible material, wherein the connecting means and the head are separate devices.

Another aspect of the present invention pertains to a member for tethered connection to a bone. Some embodiments include a bone connecting member adapted and configured for connection with a vertebra. Some embodiments include a tethering head coupled to the bone connecting member, the tethering head including a passageway being adapted and configured to accept therein a flexible tether, the tethering head including an opening providing access to said passageway, and a separate member adapted and configured to close the opening.

Yet another aspect of the present invention pertains to a member for tethered connection to a bone, including a bone connecting member and a tethering head non-integral with the bone connecting member, the tethering head including a passageway being adapted and configured to accept therein a flexible tether. The tethering head may include a bone contacting surface, wherein connection of the bone connecting member to a vertebra places the bone contacting surface in contact with the vertebra.

Still another aspect of the present invention pertains to a member for tethered connection to a bone including a bone connecting member and a tethering head separable from the bone connecting member, the head including a passageway adapted and configured to accept therein a flexible tether, the passageway being accessible from the top of the tethering head. Some embodiments include a separate cover adapted and configured to cover the passageway.

Another aspect of the present invention pertains to a member for tethered connection to a bone, some embodiments including a bone connecting member. Other embodiments include a head including first and second passageways extending across the head; each passageway being adapted and configured to accept therein a corresponding first or second tether, the head including a smoothly contoured convex lower surface that partially separates the first passageway from the second passageway.

Yet another aspect of the present invention pertains to a member for tethered connection to a bone, some embodiments including a head attached to the bone connecting member, the head including first and second spaced apart securement posts each adapted and configured for connection to a loop of a flexible tether. In some embodiments each post includes a groove sized to accept therein a tether loop.

Still another aspect of the present invention pertains to a member for tethered connection to a bone including a bone connecting member and a head attached to the bone connecting member, the head including first and second peripheral grooves each adapted and configured for connection to one or more loops of flexible tether.

Another aspect of the present invention pertains to a method for tethering of vertebrae. Some embodiments include attaching a first tethering head to a first vertebra, attaching a second tethering head to the first vertebra spaced apart from the first tethering head, and attaching a third tethering head to a second vertebra. Other embodiments of the present invention include attaching one end of a first flexible tether to the first tethering head and attaching one end of a second flexible tether to the second tethering head. Still other embodiments pertain to connecting the first vertebra to the second vertebra by looping the other end of the first flexible tether with the third tethering head.

Yet another aspect of the present invention pertains to a method for tethering of vertebrae. Some embodiments include attaching a first tethering head to a first vertebra and attaching a second tethering head to a second vertebra. Other embodiments include attaching a flexible tether to the first tethering head, and extending the tether from the first tethering head to the second tethering head and passing the extension of the looped tether though an aperture in the second tethering head.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 28 is a perspective CAD surface representation of a vertebral tethering member according to yet another embodiment of the present invention.

FIG. 29 is a side elevational view of the apparatus of FIG. 28.

FIG. 30 is an end elevational view of the apparatus of FIG. 28.

FIG. 31 is a top plan view of the apparatus of FIG. 28.

FIG. 36B shows a portion of tether having 2 free ends.

FIG. 36C shows the tether of FIG. 36B with the free ends spliced together to form an endless loop.

FIG. 36D shows the loop of FIG. 36C attached to a pair of tethering anchors.

FIG. 36E shows the portion of tether of FIG. 36B with one of the free ends spliced to an intermediate portion of the tether in a way that creates an adjustable loop, in which the size of the loop can be changed by pulling on the remaining free end.

FIG. 36F shows the loop of FIG. 36E coupled to a pair of tethering anchors spaced apart by a first distance.

FIG. 36G shows the assembly of FIG. 36F after the free end has been pulled so as to create sufficient tension in the tether and draw the 2 anchors together and spaced apart by a second distance that is less than the distance shown in FIG. 36F.

FIG. 42 is a frontal view of the apparatus of FIG. 40.

FIG. 43 is a cross sectional representation of the apparatus of FIG. 42, with the cross section taken in the plane of the figure.

FIG. 44 is a cross sectional representation of the apparatus of FIG. 42, with the cross section taken in the plane perpendicular of the figure.

FIG. 45 is a bottom plan view of the apparatus of FIG. 40.

FIG. 46 is a top plan view of the apparatus of FIG. 40.

FIG. 56 is a side, top perspective CAD surface representation of a vertebral tethering member according to yet another embodiment of the present invention, shown assembled.

FIG. 57 shows an assembled view of the apparatus of FIG. 40, shown exploded.

FIG. 58 is a top plan view of the apparatus of FIG. 56.

FIG. 59 is a bottom plan view of the apparatus of FIG. 56.

FIG. 65 is a cross sectional representation of the apparatus of FIG. 66, with the cross section taken in a plane through the centerline and parallel to the plane of FIG. 66.

FIG. 66 is a side elevational view of the apparatus of FIG. 62.

FIG. 67 is a bottom plan view of the apparatus of FIG. 66.

FIG. 68 is a top plan view of the apparatus of FIG. 66.

FIG. 69 is a top plan view of a portion of the apparatus shown in FIG. 63.

ELEMENT NUMBERING

Figure 1:
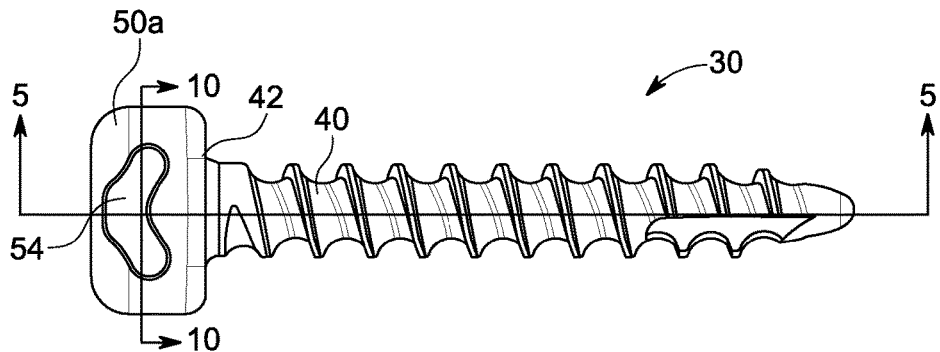
FIG. 1 is a CAD surface representation of a vertebral tethering member according to one embodiment of the present invention.

The following is a list of element numbers and at least one noun used to describe that element. It is understood that none of the embodiments disclosed herein are limited to these nouns, and these element numbers can further include other words that would be understood by a person of ordinary skill reading and reviewing this disclosure in its entirety.

| 20 | spine |
| 22 | vertebrae |
| 24 | suture or tether loop |
| 25 | rod |
| 26 | suture approach direction |
| a | guiding |
| b | hitching |
| c | looping |
| 30 | vertebral tethering member |
| a | guiding |

-continued

| b | hitching |
| c | looping |
| 32 | rod coupling member |
| 34 | suture or rod capturing member |
| a | connection feature; threads |
| 40 | means for connecting head to vertebra |
| 42 | neck |
| 44 | anchor |
| a | shaft |
| b | tip |
| c | threads |
| d | central axis |
| e | cannula |
| 46 | plates |
| a | through holes; fastener holes |
| b | bone contacting surface |
| c | upper surface |
| 47 | anchoring head |
| a | driving feature |
| b | compression surface |
| c | undersurface |
| 50 | tethering head |
| a | guiding head |
| b | hitching head |
| c | looping head |
| 52 | planform shape; oblong; circular |
| a | maximum width |
| b | central width |
| c | driving feature |
| d | smooth outer surface |
| e | underside; bone contacting surface |
| f | top surface |
| g | plane of symmetry |
| h | plane of symmetry |
| i | compression surface |
| j | bone interface projections |
| k | larger diameter cylindrical aperture; well; head receiving and locating surface |
| l | smaller diameter cylindrical aperture |
| m | head o.d. clearance cylindrical surface |
| 54 | passageways |
| a | entrance |
| b | exit |
| c | width, entrance to exit |
| d | inner wall |
| e | first passageway |
| f | second passageway |
| h | top wall |
| i | bottom wall |
| j | ears |
| 56 | floor |
| a | convex feature |
| b | V-shape |
| c | included angle |
| d | ridge |
| 57 | suture capturing member |
| 60 | looping head |
| 64 | peripheral groove |
| a | top |
| b | bottom |
| c | width |
| d | depth |
| 70 | hitching head |
| 73 | slot or opening |
| a | width |
| 74 | securement post |
| a | maximum width |
| b | radiused edges |
| c | overhang |
| d | minimum cross sectional area |
| e | angular extent |
| f | first |
| g | second |
| h | post angle, tether approach |

DETAILED DESCRIPTION OF ONE OR MORE EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention, and further permits the reasonable and logical inference of still other embodiments as would be understood by persons of ordinary skill in the art.

It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims. The usage of words indicating preference, such as "preferably," refers to features and aspects that are present in at least one embodiment, but which are optional for some embodiments, it therefore being understood that use of the word "preferably" implies the term "optional."

The use of an N-series prefix for an element number (NXX.XX) refers to an element that is the same as the non-prefixed element (XX.XX), except as shown and described. As an example, an element 130 would be the same as element 30, except for those different features of element 130 shown and described. Further, common elements and common features of related elements may be drawn in the same manner in different figures, and/or use the same symbology in different figures. As such, it is not necessary, as one example, to describe features of 154 and 54 that are the same, since these common features are apparent to a person of ordinary skill in the related field of technology. Further, it is understood that some features may be backward compatible, such that a feature of a later discussed embodiment (NXX.XX) may include features compatible with other various embodiments that were discussed earlier (MXX.XX), as would be understood by those of ordinary skill in the art. This description convention also applies to the use of prime ('), double prime ("), and triple prime ('") suffixed element numbers. Therefore, it is not necessary to describe the features of 20.1, 20.1', 20.1", and 20.1'" that are the same, since these common features are apparent to persons of ordinary skill in the related field of technology.

This document may use different words to describe the same element number, or to refer to an element number in a specific family of features (NXX.XX). It is understood that such multiple, different words are not intended to provide a redefinition of any language herein. It is understood that such words demonstrate that the particular feature can be considered in various linguistic ways, such ways not necessarily being additive or exclusive.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise explicitly noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

Various embodiments of the present invention pertain to different methods and apparatus for providing a flexible connection among the vertebra of a spine, and also different methods for providing a connection between a vertebra and a rod. Various tethering heads are shown which provide one or more of a looping attachment of one or more suturing loops, guidance of the suture loop over several vertebrae, or the hitching attachment of multiple suturing loops. Each of the tethering heads can include any acceptable means for attachment to a vertebrae. Examples shown herein include screw-type bone anchors and fastener-coupled bone plates. However, the tethering heads and tethering methods discussed herein can be attached by any method.

Further shown herein are various methods for using one or more of the tethering heads in combination on a particular patient. As examples, looping-type or hitching-type tethering heads can be utilized for attachment of the loop itself to the tethering head. Various methods contemplate multiple tethering heads being attached to one vertebrae, and connected or guided with a single tethering head on an adjacent vertebrae. As will be shown, the tethering heads discussed herein permit the simultaneous use of one or more suturing loops across one or more vertebrae.

In some of the present invention include tethering members that include one piece, unitary devices incorporating both a tethering head and an anchoring means. However, yet other embodiments contemplate separation of the two functions, such that the tethering head is attached to a vertebra by a separate anchoring means, such as a screw, pin, plate, or other device disclosed herein.

Figure 2:
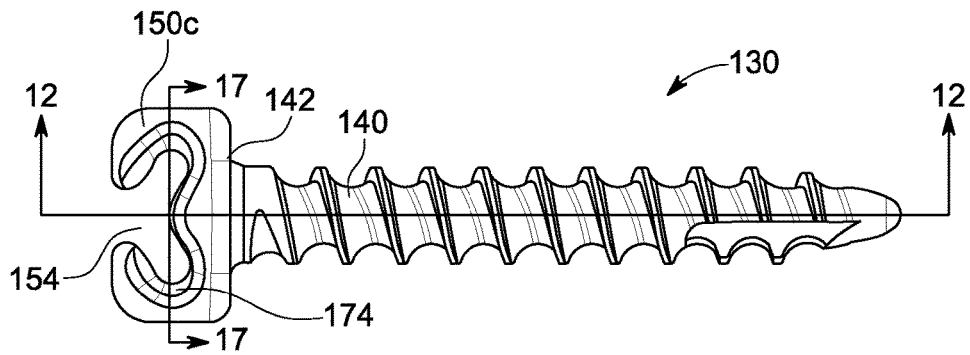
FIG. 2 is a CAD surface representation of a vertebral tethering member according to yet another embodiment of the present invention.
Figure 3:
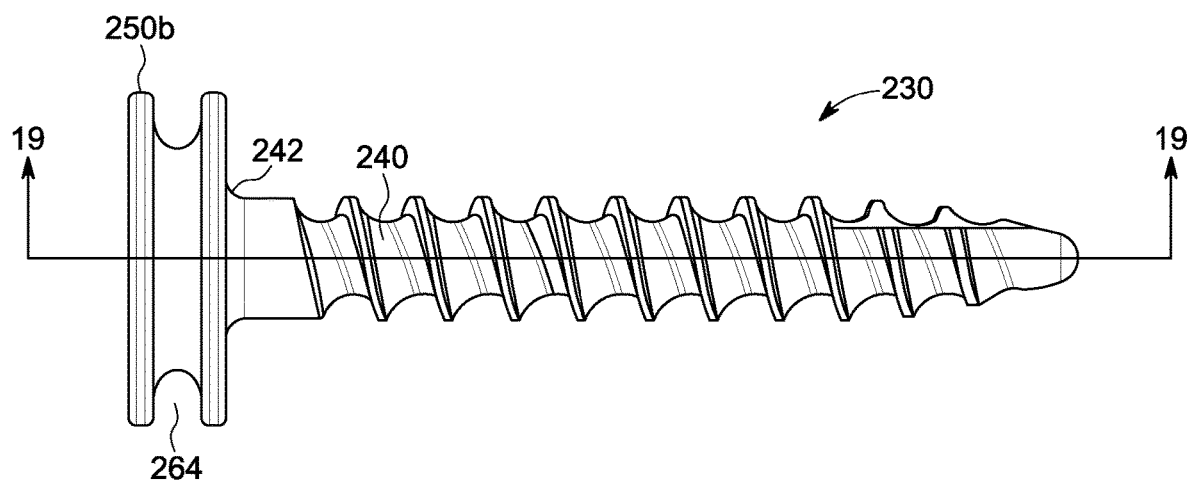
FIG. 3 is a CAD surface representation of a vertebral tethering member according to yet another embodiment of the present invention.
Figure 4:
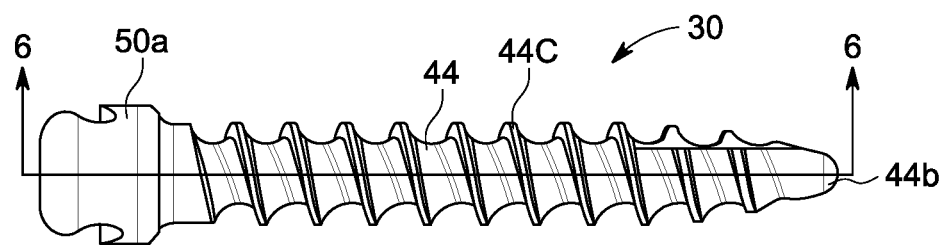
FIG. 4 is a side elevational view of the apparatus of FIG. 1.

FIGS. 1, 2, and 3 show side elevational views of vertebral tethering members 30, 130, and 230, respectively, each having tethering heads X50 according to various embodiments of the present invention. FIG. 1 shows a tethering head 50*a* that is adapted and configured to guide within the head the strands of a loop of tethering or suturing material. FIG. 2 presents a side elevational view of a tethering head 150*c* adapted and configured to provide one or more "hitching" posts that are adapted and configured to receive around each of them a loop of tethering or suturing material. FIG. 3 shows a tethering head 250*b* adapted and configured to receive in a groove around its periphery a loop of tethering or suturing material. Unless otherwise stated, the various tethering heads X50 disclosed herein provide securement of the flexible tether to the head, but preferably without compressing, abrading, or restricting the movement of the flexible tether within the various passageways X54.

FIGS. 1 and 4-10 show various views of a vertebral tethering member 30 according to one embodiment of the present invention. Tethering member 30 includes a tethering head 50*a* and means 40 for connecting the head to a vertebrae. Tethering head 50*a* includes within it an upside down, enclosed V-shaped passageway 54. In the embodiment shown, connecting means 40 is an anchoring screw 44 that includes a plurality of threads 44*c* on a shaft 44*a*. Connecting means 40 extends from a neck 42 that attaches to the underside of head 50*a* to a tip 44*b* that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52*e* of the head 50.

Figure 5:
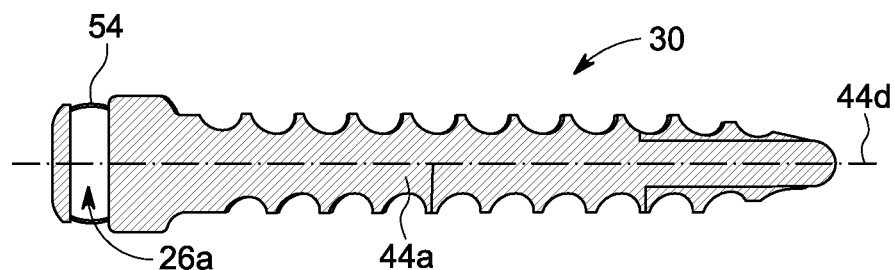
FIG. 5 is a cross sectional representation of the apparatus of FIG. 1 as taken along line 5-5 of FIG. 1.
Figure 6:
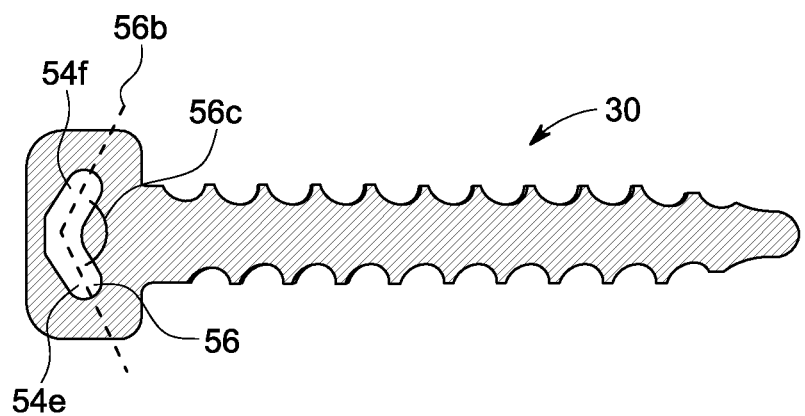
FIG. 6 is a cross sectional representation of the apparatus of FIG. 1 as taken along line 6-6 of FIG. 4.
Figure 7:
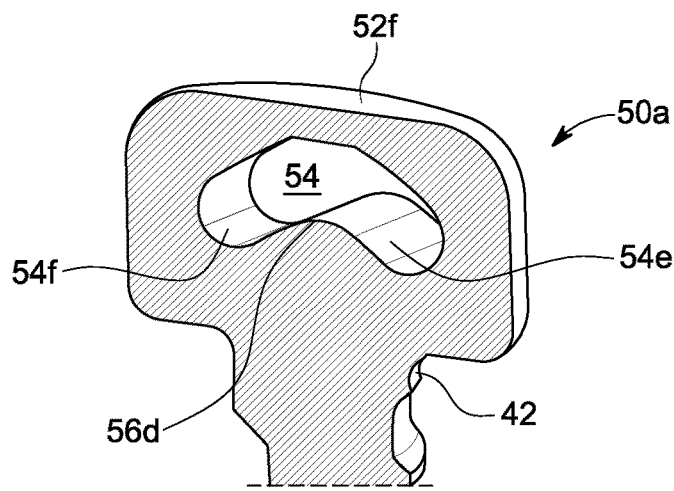
FIG. 7 is a cross sectional, perspective, and enlarged representation of a portion of the apparatus of FIG. 6.

Tethering head 50*a* includes within it a passageway 54, as best seen in FIGS. 5, 6, and 7. In some embodiments, this larger passageway 54 includes separated first and second passageways 54*e* and *f*, preferably arranged in a V-shape. Although as shown in FIGS. 6 and 7, the V-shape is "upside down" (with the vertex of the V being proximate to the top surface 52*f* of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Figure 9:
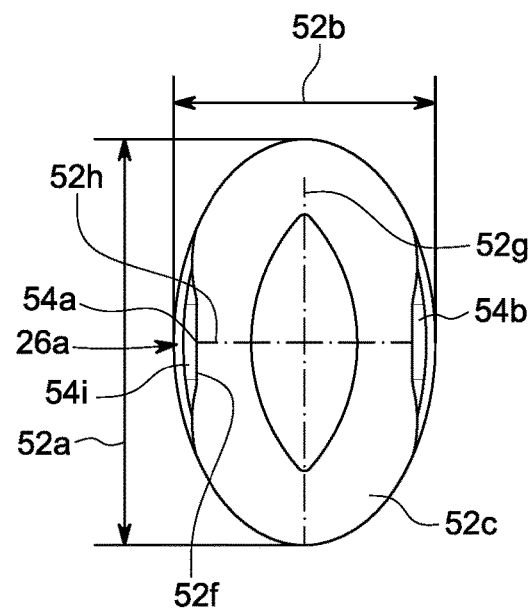
FIG. 9 is a top plan view of the apparatus of FIG. 1, looking from the head toward the shank.

Passageways 54*e* and 54*f* are adapted and configured to permit the passage therethrough of the 2 strands of a single continuous (or endless) loop of tethering material. The end of the loop and the strands of the loop are provided to the entrance 54*a* of the passageways, and leave the passageway through exit 54*b* (referring to FIG. 9). It is understood that the terms entrance and exit are used for convenience, and that the loop and strands can be entered or exited through either side. Referring to FIG. 9, it can be seen that the shape 52 of head 50 is symmetric about the two planes 52*g* and 52*h* as shown. However, other embodiments of the present invention contemplate shapes of tethering heads that have only a single plane of symmetry, or no symmetry at all. In such embodiments, one of the entrance and exit may have one or more distinctly different features than the other of the entrance or exit.

Referring to FIG. 7, in some embodiments the passageways 54*f* and 54*e* are separated by a convex feature 56*a* located on the floor 56 of the passageway. In the embodiment shown, the convex feature 56*a* is a ridge 56*d* that extends generally across the width 52*b* of the head 50*a*. Referring to FIGS. 6 and 7, this central ridge can be seen to generally follow the upside down V-shape 56*b*, except with substantially smooth, rounded contours. These smooth and rounded contours of the floor (as well as elsewhere in the various passageways and shapes of the heads X50 shown herein) are useful in minimizing stress concentrations, and which would otherwise arise in the tethering material, and which could otherwise result in abrasion and potential failure of the tethering material. Although the convex feature 56*a* of floor 56 is shown as a ridge 56*d* (in FIG. 7), it is also understood that the convex floor need not extend across the entire width of the passageway, and as another example could be one or more bumps in the floor. It is also understood that other features (such as a convex ceiling of the passageway) could also provide separation of the laterally opposed passageways 54*e* and 54*f*.

Referring to FIG. 9, it can be seen that in some embodiments the tethering head 50*a* has a smooth outer peripheral surface 52*d* and top surface 52*f*. In the embodiments shown, the head 52 has an oblong shape, with a maximum width 52*a* and a central width 52*b*. As shown in FIG. 9, in some embodiments all peripheral sides of the planform of the head are rounded and smooth so as to minimize abrasion of the tethering loops.

Figure 10:
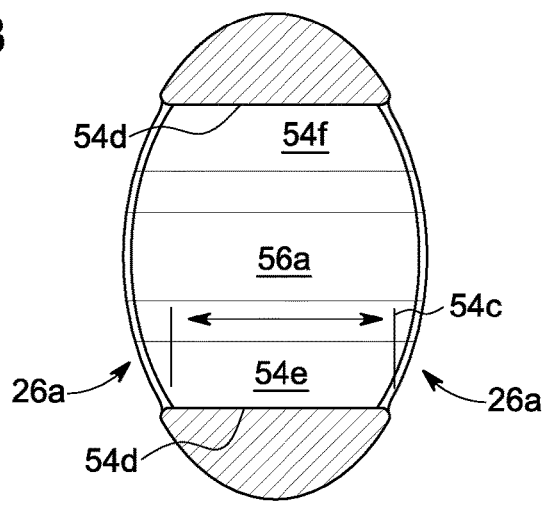
FIG. 10 is a cross sectional view of the apparatus of FIG. 1 as taken along line 10-10 of FIG. 1.
Figure 11:
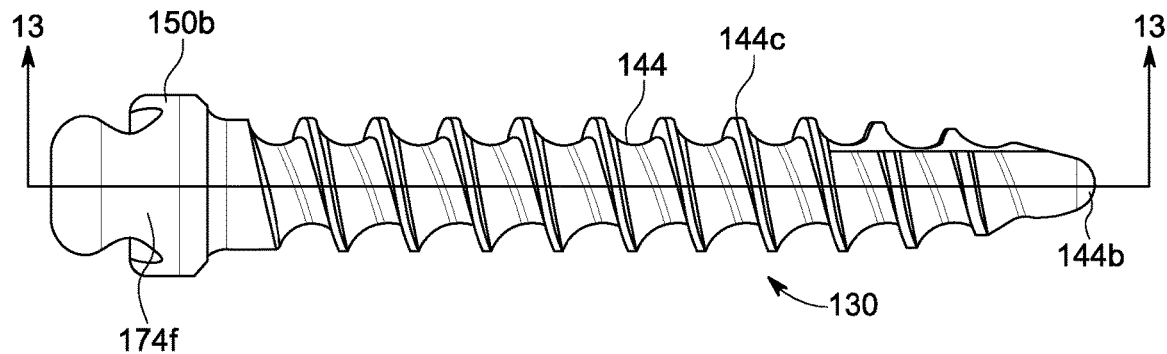
FIG. 11 is a side elevational view of the apparatus of FIG. 2.
Figure 12:
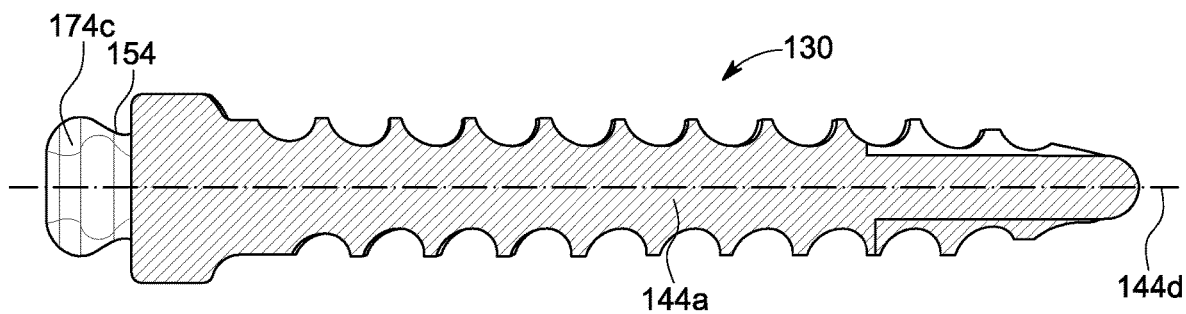
FIG. 12 is a cross sectional representation of the apparatus of FIG. 2 as taken along line 12-12 of FIG. 2.

Comparing FIGS. 9 and 10, it can be seen that the opposing inner walls 54*d* of the passageway have a width 54*c* from entrance to exit that is less than the central width 52*b* of the head shape 52, a result at least in part of the oblong planform shape 52 of the head. In addition, referring to FIG. 9, it can be seen that the top 52*f* of the head proximate to central plane 52*h* is slightly relieved inwardly relative to the bottom surface 54*i*. This slight pullback of the passageway entrance and exit from the edges of the head, combined with the use of an oblong shape in which the passageway cuts through the smaller width of the oblong shape, allows for a wider variation in the approach and departure directions of the loop relative to the passageways.

FIGS. 5, 9 and 10 provide examples of the approach and departure directions of the suture loop relative to head 50*a*. Preferably, the suture direction 26*a* is generally through passageway 54, and across the central width 52*b*. The approach direction 26*a* shown in FIG. 5 schematically represents this direction, yet the head 50*a* is adapted and configured such that the approach need not be orthogonal to any particular feature, centerline or symmetry plane of the head. FIG. 9 and FIG. 10 illustrate various approach and departure directions that are acceptable by considering the many smooth, contoured features of the overall head shape, as well as the features previously discussed relative to the entrance and exit of the passageway.

FIGS. 2 and 11-18 show various views of a vertebral tethering member 130 according to another embodiment of the present invention. Tethering member 130 includes a tethering head X50*b* and means 40 for connecting the head to a vertebrae. Tethering head 150*b* includes within it an upside down, enclosed V-shaped passageway 154. In the embodiment shown, connecting means 140 is an anchoring screw 44 that includes a plurality of threads 44*c* on a shaft 44*a*. Connecting means 40 extends from a neck 42 that attaches to the underside of head 50*b* to a tip 44*b* that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52*e* of the head 50.

Tethering head 150*b* includes within it a passageway 154, as best seen in FIGS. 5, 6, and 7. In some embodiments, this larger passageway 154 includes separated first and second passageways 154*e* and *f*, preferably arranged in a V-shape.

Figure 8:
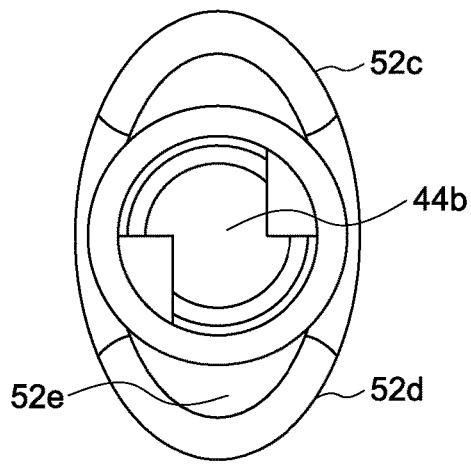
FIG. 8 is a bottom plan view of the apparatus of FIG. 1, looking from the shank toward the head.

Although as shown in FIGS. 6 and 7, the V-shape is "upside down" (with the vertex of the V being proximate to the top surface 152f of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Vertebral tethering member 130 includes a "hitching" or looping-connection head 150b. Comparing FIGS. 13 and 6, it can be seen that the head 150b includes a passageway 154 that looks similar to the passageway 54, except that a slot or opening 73 extends across the top surface 152f. Other similarities between member 130 and member 30 can be seen, such as the passageways 154e and 154f on opposite sides of head 150b, with the passageways being angled in an approximate V-shape 156b, with the included angle 156c of the V-shape being preferably greater than about ninety degrees. Further in comparison of FIGS. 13 and 6, it can be seen that the floor 156 includes a convex feature 156a that roughly parallels the V-shape with a smooth ridge 156d.

One difference between a tethering head X50a and a tethering head X50b is the manner in which the head interfaces with the suture loop. As previously discussed, a tethering head X50a is adapted and configured to guide within it the strands of a tether loop. The tether has an approach direction 26a that in some embodiments has the loop passing through a pair of exits (on lateral sides of the passageway) and a pair of exits (also on corresponding lateral sides of the passageway).

Figure 13:
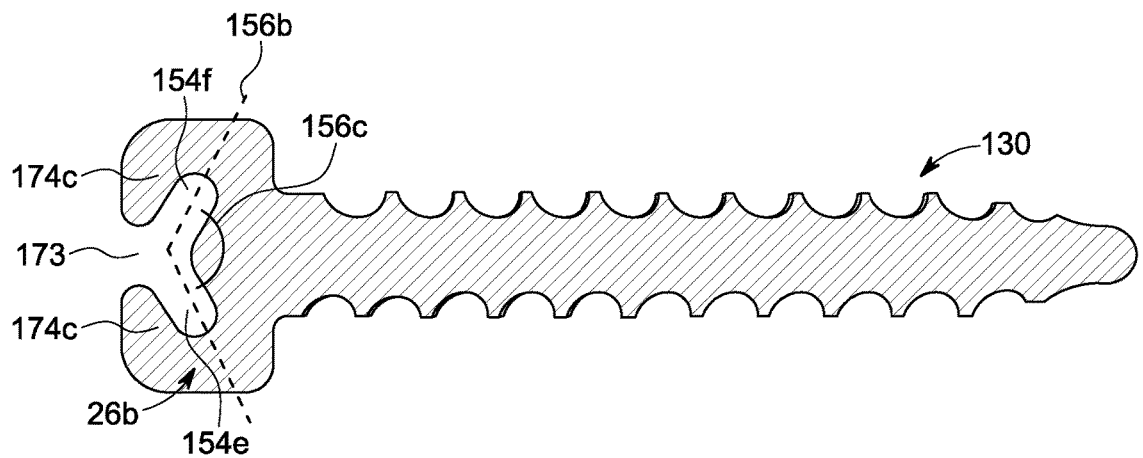
FIG. 13 is a cross sectional representation of the apparatus of FIG. 1 as taken along line 13-13 of FIG. 11.
Figure 17:
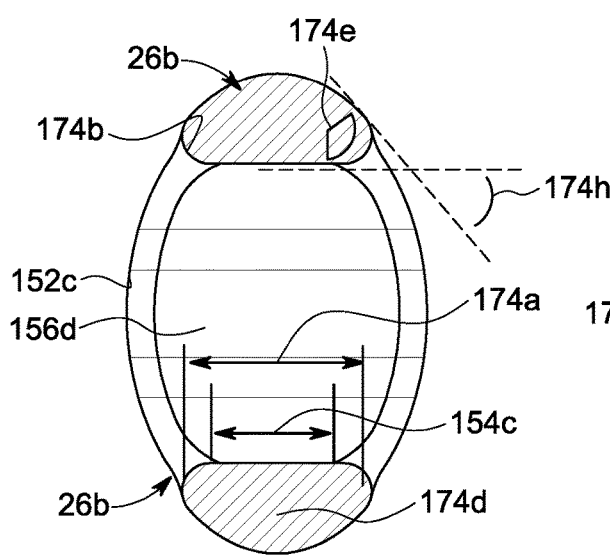
FIG. 17 is a cross sectional view of the apparatus of FIG. 2 as taken along line 17-17 of FIG. 2.

In comparison, a tethering head X50b in some embodiments contemplates a suture loop approaching direction 26b (referring briefly to FIGS. 15 and 17) that is generally orthogonal to the approach direction 26a. As best seen in comparing FIGS. 14 and 16 to FIGS. 7 and 9, respectively, is that a tethering head X50b is adapted and configured to be loopingly connected (or hitched) to a post X74 of the head X50b. Referring briefly to FIGS. 13 and 17, it can be seen that the suture approach direction 26b is in a direction generally orthogonal to the approach direction 26a for a head 50a, as seen in FIGS. 5 and 10.

Figure 14:
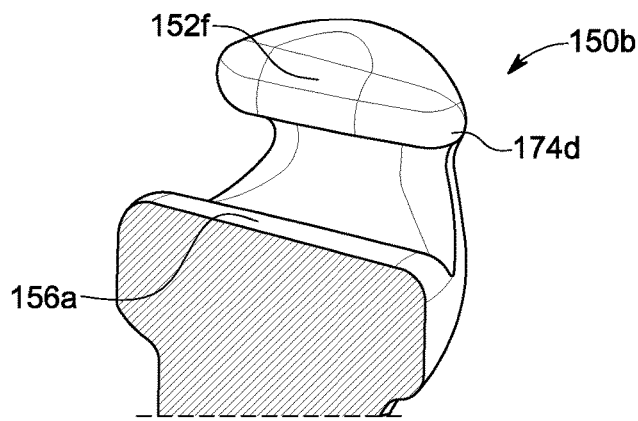
FIG. 14 is a cross sectional, perspective, and enlarged representation of a portion of the apparatus of FIG. 13.
Figure 15:
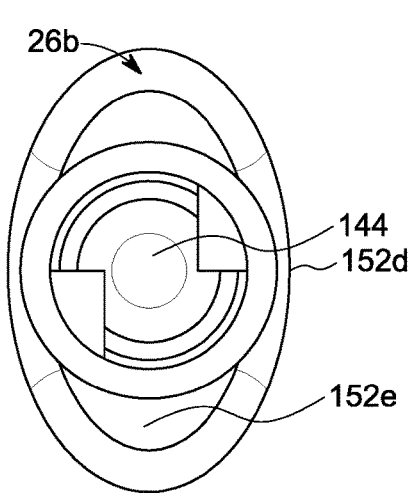
FIG. 15 is an end plan view of the apparatus of FIG. 2, looking from the shank toward the head.
Figure 16:
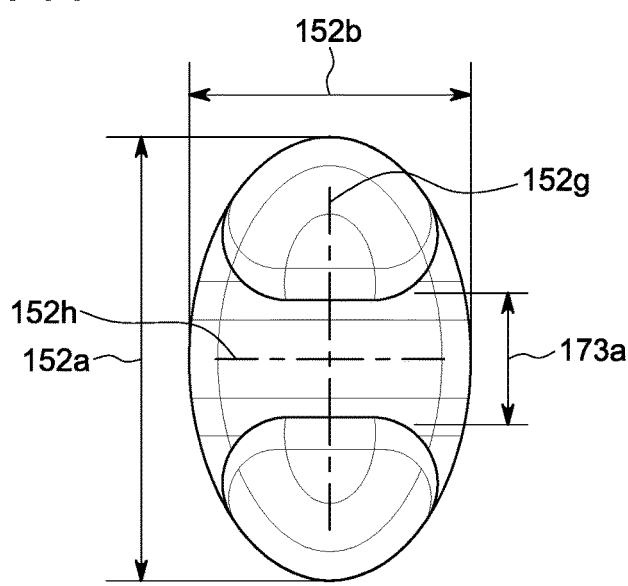
FIG. 16 is a top plan view of the apparatus of FIG. 2, looking from the head toward the shank.
Figure 18:
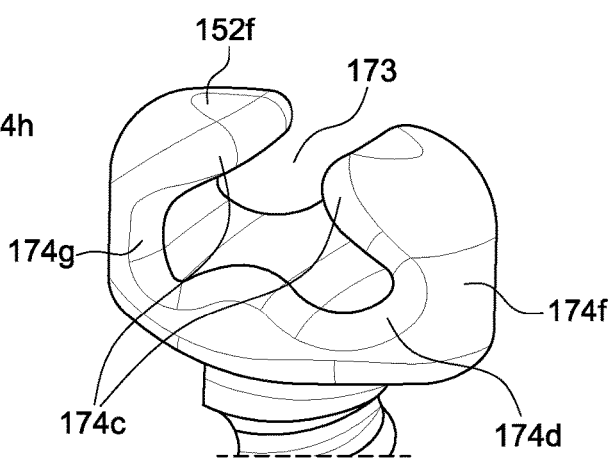
FIG. 18 is an enlarged perspective view of a portion of the apparatus of FIG. 2.

Yet another difference between a tethering head X50a and a tethering head X50b is the placement of a slot 173 that extends through the top surface 152f of a head X50b. This slot 173 preferably has a width 173a and also smoothing and contouring features that adapt it and configure it to permit downward passage of a loop of suture. Referring to FIG. 14 and FIG. 18, it can be seen that the slot, combined with preferably significantly radiused edges 174b proximate to a minimum cross sectional area 174d, in combination with passageways 154e and 154f, create first and second suture loop hitching posts 174f and 174g.

A tethering head X50b according to various embodiments of the invention is attached to an undercut location along either of two laterally facing posts 174f or 174g. Comparing FIGS. 13 and 17, it can be seen that the suture loop approach direction 26b does not have to be at a right angle (as suggested by FIG. 13) but can be at any angle (as shown in FIG. 17) that still permits the loop to be protectively retained under the overhang 174c of the attachment post 174.

FIG. 17 shows additional features that permit a variety of approach directions toward the hitching post 174. As one example, it can be seen that the width of the passageway 154c is shorter than the maximum width 174a of the post (as shown toward the bottom of FIG. 17). A radiused edge 174b transitions from width 154c of the inner wall 154d to the maximum width 174d. This radius 174b is adapted and configured to eliminate or minimize any stress concentration in the suture loop as it wraps around the corner 174b. FIG. 17 also shows that the angular extent 174e defined between the tangent lines 174h is in excess of ninety degrees. Comparing FIGS. 15 and 17, it can be seen that the radiused corners 174b and angular extent 174e of the entrance or exit permits a variety of suture approach directions that can differ significantly from the plane 152g that includes the major axis of the oblong head.

These various contouring features described above, along with the slot 173 and V-shape 156b, also combine to create an overhanging portion 174c for each post. This overhanging portion 174c (best seen in FIGS. 13 and 18) extends from the respective post in a direction generally opposite to the direction of tension that would be applied to the suture loop. Because of this overhang, any attempt at vertical movement of the suture loop is discouraged, since any movement of the suture loop away from the minimal cross sectional area 174d and toward the overhand 174c would require increased tension in the loop, and thus resist the attempted vertical movement. Therefore, the placement of the minimum cross sectional area between the overhand 174c and the floor convex feature 158 discourages top to bottom movement of the loop, and encourages placement of the loop around the minimum cross sectional area.

FIGS. 3 and 19-22 show various views of a vertebral tethering member 230 according to another embodiment of the present invention. Tethering head 250c includes around it one or more peripheral grooves 264 that are adapted and configured to receive within them a tether that is looped around the periphery. In the embodiment shown, connecting means 240 is an anchoring screw 44 that includes a plurality of threads 44c on a shaft 44a. Connecting means 40 extends from a neck 42 that attaches to the underside of head 50a to a tip 44b that is adapted and configured to be inserted into a hole in the vertebrae. The necks X42 shown herein preferably include increased cross sectional areas proximate to this attachment, so as to manage the distribution of stresses and forces transitioning between the head and the connection means.

As shown and described herein, means X40 for connecting a head X50 to a vertebrae can be any type of device or method that securely affixes the head X50 to the vertebrae. Examples include the anchoring screws shown in several embodiments herein, as well as a plate, post, hook, clip, or strap, as examples. In the embodiments shown, the connection means 40 includes a neck X42 that provides attachment to the underside 52e of the head 50.

Figure 19:
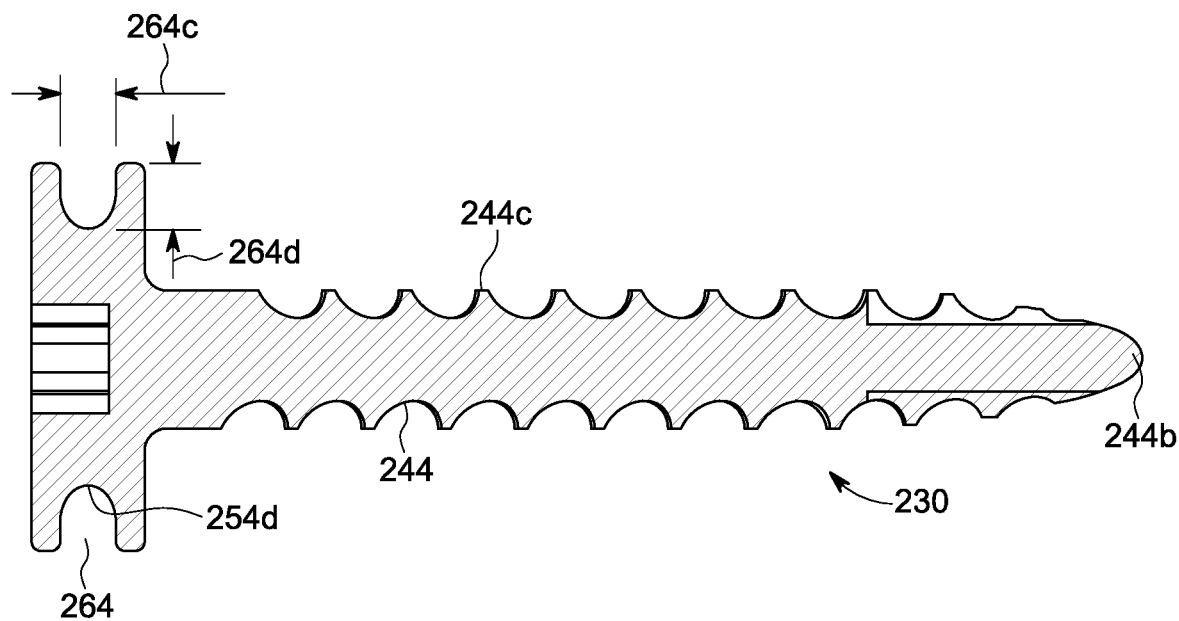
FIG. 19 is a cross sectional representation of the apparatus of FIG. 3 as taken along line 19-19.
Figure 20:
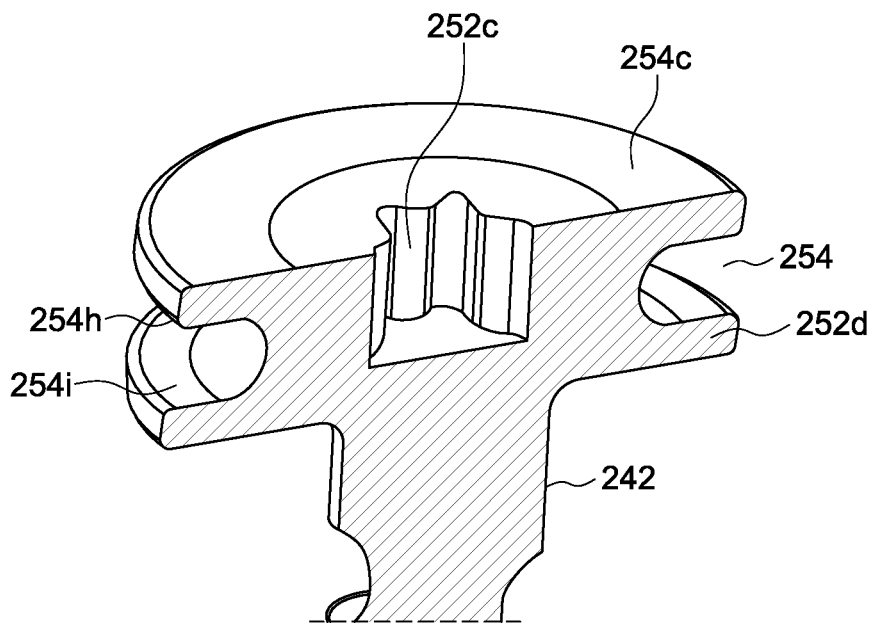
FIG. 20 is a perspective view of a portion of the apparatus of FIG. 19.

Vertebral tethering member 230 includes a tethering head 250c adapted and configured for looping connection to a flexible tether or suture. Referring to FIG. 19, it can be seen that a tethering head X50c preferably includes a peripheral groove 264 that extends around the smooth outer surface 252d of head 250c. In one embodiment, this groove is recessed into the periphery, with the inner wall 254d of the groove being smoothly contoured and rounded for minimal abrasion with a suture loop placed within the groove. In one embodiment, as shown in FIG. 19, the inner wall 254d has a semi-circular shape, although other embodiments of the present invention contemplate smoothly contoured and rounded walls of any shape, including walls having elliptical cross sections and parabolic cross sections as examples.

Preferably, the groove includes a top and bottom pair of walls 254h and 254i, respectively that, combined with the innermost wall 254d, form the suture loop passageway 254. Preferably, this passageway has a width 264c greater than the unstressed diameter of the suture material, as well as a depth 264d greater than the unstressed diameter of the suture material. By having groove dimensions greater than the unstressed diameter, the physician will easily wrap the unstressed loop around and into passageway 254, and preferably without the need to push or force the suture material into the groove. However, yet other embodiments of the present invention contemplate a groove 264c in which the unstressed material fits tightly and securely within the groove.

In a manner similar to the post overhangs 174c previously discussed, the top and bottom surfaces 254h and 254i, combined with the depth 264d of passageway 254, result in the implanted suture remaining securely within the groove, and not escaping the groove even if the tension on the suture is slightly relieved. The overhang of the top and bottom walls 254h and 254i also provide protection to the suture loop within groove 254 from abrasion from other nearby features.

Figure 21:
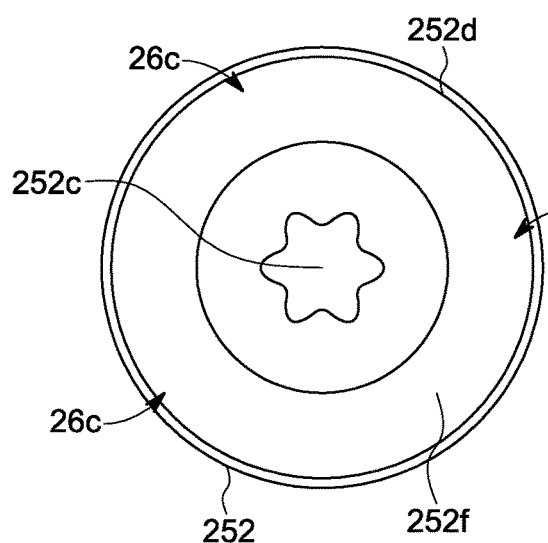
FIG. 21 is a top plan view of the apparatus of FIG. 3 of the head looking toward the shaft.

It is noted that the suture placed within groove 264 should be large enough to fit over the peripheral shape 252 of the head 250c, as best seen in FIG. 21. Comparing head 250c and 150b (shown in FIG. 16), it can be seen that the loop of suture material for head X50b should be large enough to fit over the top surface 152f of a post 174.

Figure 23:
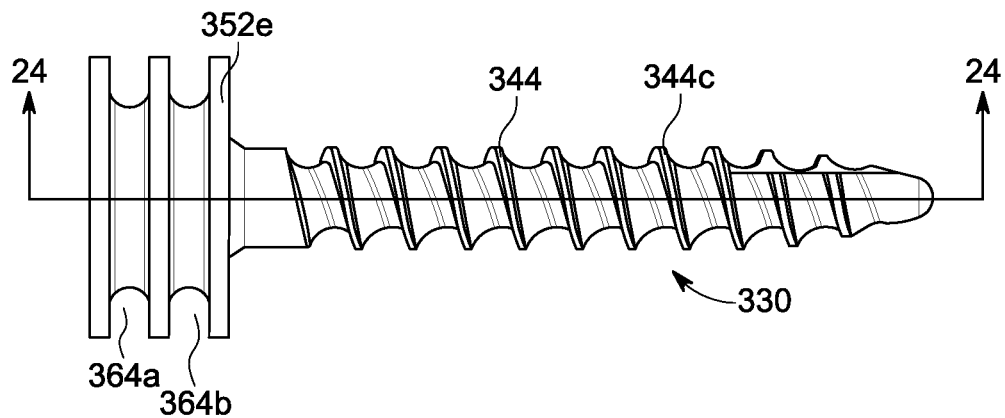
FIG. 23 is a CAD surface representation of a vertebral tethering member according to yet another embodiment of the present invention.
Figure 24:
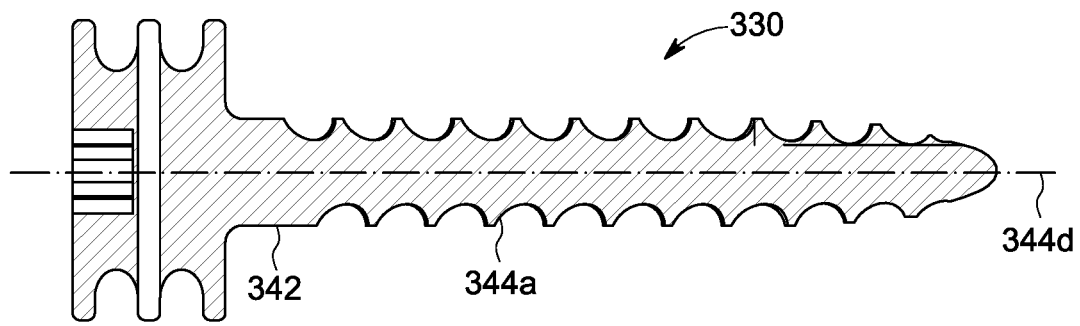
FIG. 24 is a cross sectional view of the apparatus of FIG. 23 as taken along line 24-24 of FIG. 23.
Figure 25:
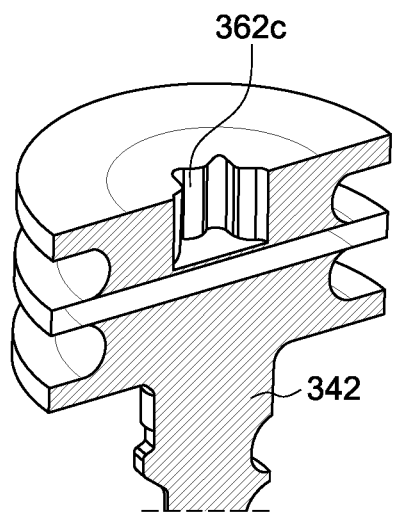
FIG. 25 is a perspective, enlarged view of a portion of the apparatus of FIG. 24.

FIGS. 23, 24, and 25 depict various aspects of a vertebral tethering member 330 similar to the member 230 previously discussed. Member 330 is similar to member 230, except including a pair of spaced apart peripheral grooves 364a and 364b. Preferably, these grooves are spaced apart vertically from the underside, bone contacting surface 352e. Member 330 permits a single tethering member to apply tension in two different directions, each direction being provided by a different suture loop.

Figure 26:
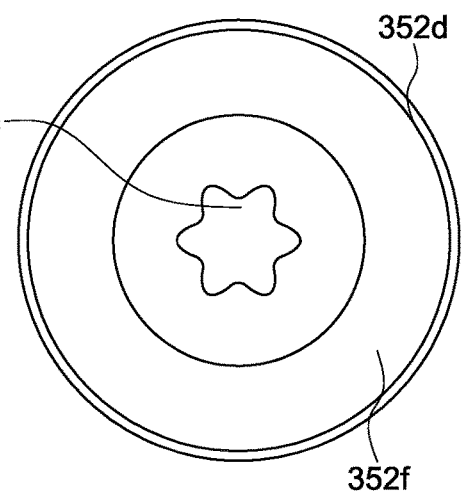
FIG. 26 is a top plan view of the apparatus of FIG. 23 from the head looking toward the shaft.
Figure 22:
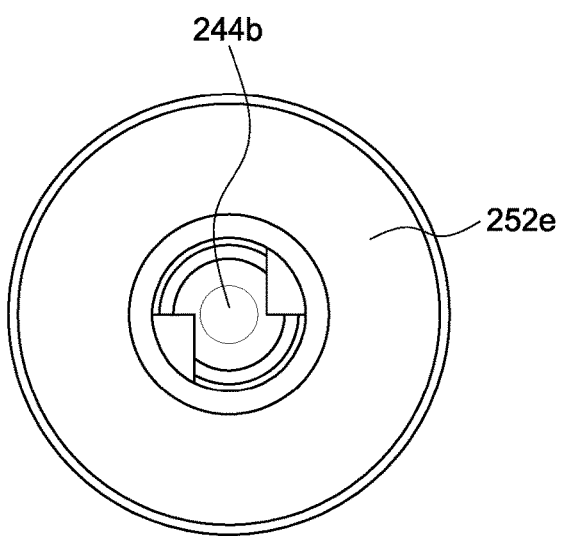
FIG. 22 is a bottom plan view of the apparatus of FIG. 3 of the shaft looking toward the head.
Figure 27:
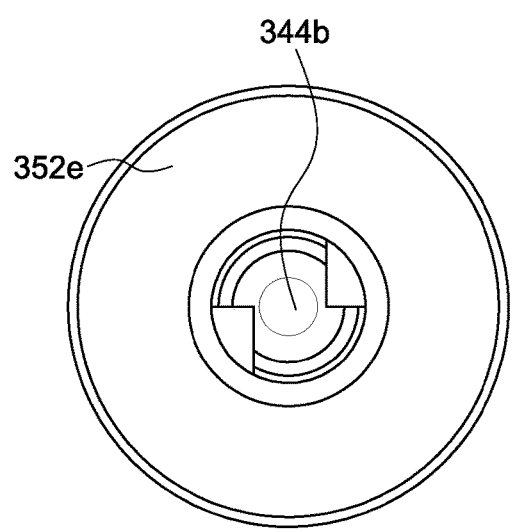
FIG. 27 is a bottom plan view of the apparatus of FIG. 23 from the shaft looking toward the head.

FIGS. 21 and 22 show top and bottom views, respectively, of tethering member 230. FIGS. 26 and 27 show similar top and bottom views, respectively, of tethering member 330. Each tethering member includes a central driving feature 252c for applying torque to the tethering member. Further, both tethering members permit a variety of suture approach directions 26c, as shown with FIG. 21. The strands of the suture can exit radially outwardly in any direction. Still further, a strand (and not a complete loop) can be wrapped part way around the groove, and depart (or approach) a head X50c tangentially to the groove, as expressed by the arrow 26c of FIG. 21 shown at about the three o'clock position. It is understood that the tethering member 330, as discussed above, is adapted and configured to provide connection to two different suture loops, each approaching in two different directions, and in any of the manners discussed with regard to tether member 230.

FIGS. 28-30 show various views of a vertebral tethering member 430 according to one embodiment of the present invention. Tethering member 430 includes a tethering head 50a and means 40 for connecting the head to a vertebrae. Tethering head 50a includes within it two, enclosed, separated passageways 454.

In the embodiment shown, connecting means 440 is a plate adapted and configured to be attached by a plurality of vertebral anchors (not shown) to a vertebrae. Connecting means 440 has a generally rectangular planform shape and includes a plurality of through holes 446a adapted and configured for securement of the plate 446 to the vertebrae by the connecting means. Although what is shown and described is a rectangular plate having four evenly spaced holes for fasteners, it is understood that the shape of plate 446 can be of any type adapted and configured for attachment to a vertebrae.

Tethering member 430 includes a guiding head X50a adapted and configured for providing passage therethrough of a suture loop. Head 450a includes a pair of spaced apart passageways 454f and 454e separated completely by a ridge 456d. Referring to FIGS. 28, 30 and 31, it can be seen that the entrance and exit of the passageways are rounded and smoothly contoured to permit a variety of suture approach directions 26a, with minimal or no abrasion to the suture loop.

In some embodiments, each passageway 454e or 454f can provide guidance therethrough for both strands of a suture loop. In yet other embodiments, the individual strands of the suture loop are separated, with one strand passing through each of the passageways. In still further embodiments, it is understood that a single passageway 454e or 454f can be sized and adapted and configured to permit passage therethrough of multiple loops, single strands of different loops, or combinations thereof.

Figure 32:
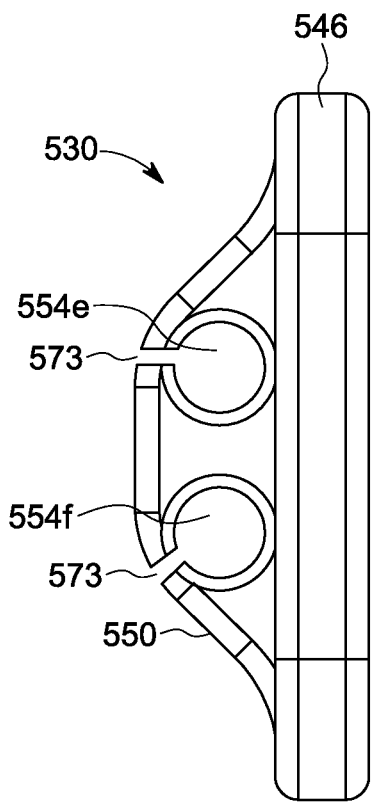
FIG. 32 is a side elevational view of a vertebral tethering member according to yet another embodiment of the present invention.
Figure 33:
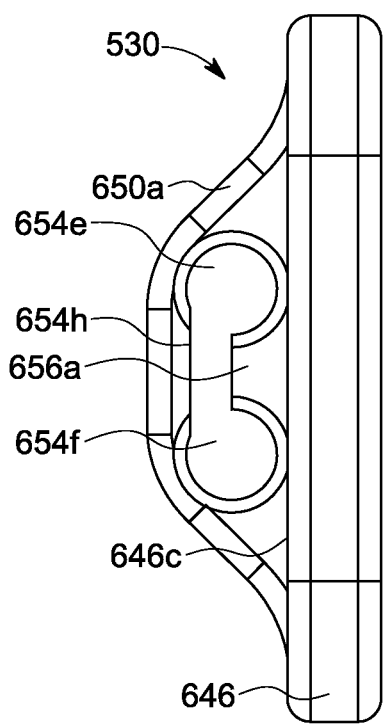
FIG. 33 is a side elevational view of a vertebral tethering member according to yet another embodiment of the present invention.
Figure 34:
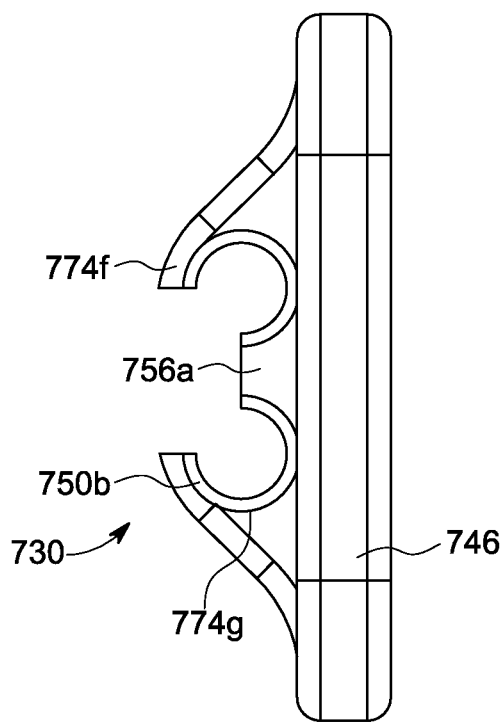
FIG. 34 is a side elevational view of a vertebral tethering member according to yet another embodiment of the present invention.

FIGS. 32, 33, and 34 depict yet further embodiments of the present invention, each including in the example shown a plate X46 for attachment of the tethering head to the vertebrae. FIG. 32 is a side elevational view of a tethering member 530 which is similar to tethering head 430 as shown and discussed. However, each of the passageways 554e and 554f include respective slots 573 that permit a suture loop to be passed into the corresponding passageway.

FIG. 33 shows a side elevational view of a vertebral tethering member 630 according to another embodiment of the present invention. Tethering member 630 is similar to tethering member 430 previously shown and discussed. However, tethering head 630 includes a convex feature 656a extending generally from a first surface 646c of plate 646, but not extending completely to the top wall 654h of head 650a. The cross sectional shape of head 650a as shown in FIG. 33 is similar in function to the fastener head 50a previously shown and discussed with regards to tethering member 30. However, it is appreciated that the cross sectional shape of the passageways is more of a figure-8 or barbell shape.

FIG. 34 shows a side elevational view of a tethering member 730 according to another embodiment of the present invention. Tethering member 730 includes connection means 740 comprising a plate 746 similar to that shown and discussed with regards to embodiment 430. However, member 730 includes a hitching-type tethering head 750b having function similar to that of anchor 130 previously discussed. Head 750b is adapted and configured to provide a pair of spaced apart posts 774f and 774g having function similar to the aforementioned hitching post.

FIGS. 35-39 depict the implantation and usage of the vertebral tethering members X30 described herein. As will be shown and discussed, various combinations of different tethering members X30 can be attached to adjacent vertebrae, or to the same vertebrae. A plurality of the tethering members X30 can be interconnected to one or several other tethering members X30. Further, these tethering interconnections can be accomplished with one or multiple loops of suturing or tethering material.

Figure 35:
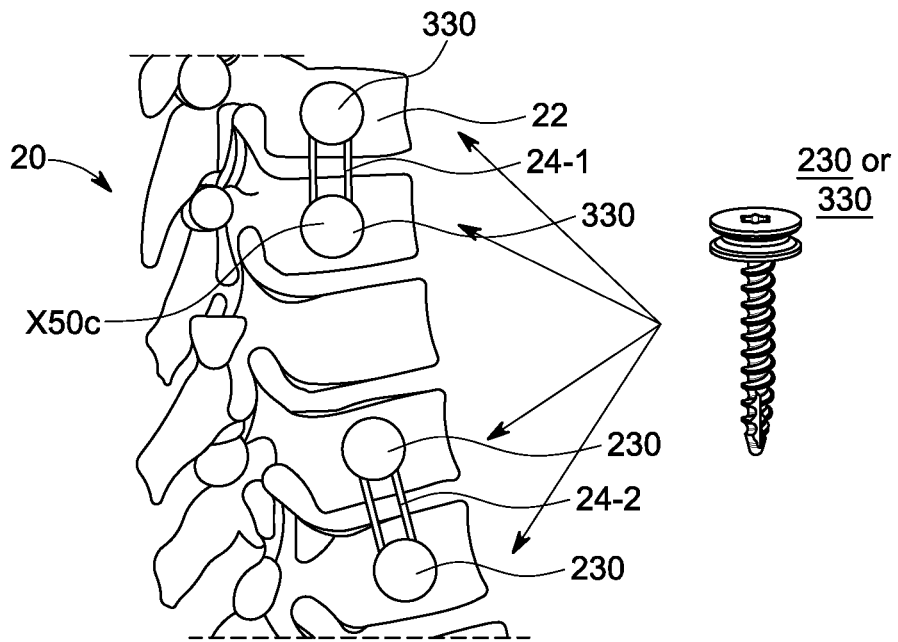
FIG. 35 is a schematic representation of an arrangement of vertebral tethering members and sutures according to another embodiment of the present invention.

FIG. 35 shows a plurality of looping connection tethering members 230 and/or 330. In the top portion of FIG. 35, a pair of tethering members 330 are shown coupled to adjacent vertebrae 22 of a spine 20. A single suture loop 24-1 is shown interconnecting the two tethering heads X50c. At the bottom of FIG. 35, a second, separate tethering loop 24-2 is shown looped around the peripheral grooves 264 of vertebral tethering members 230, each secured to different vertebrae.

Figure 36A:
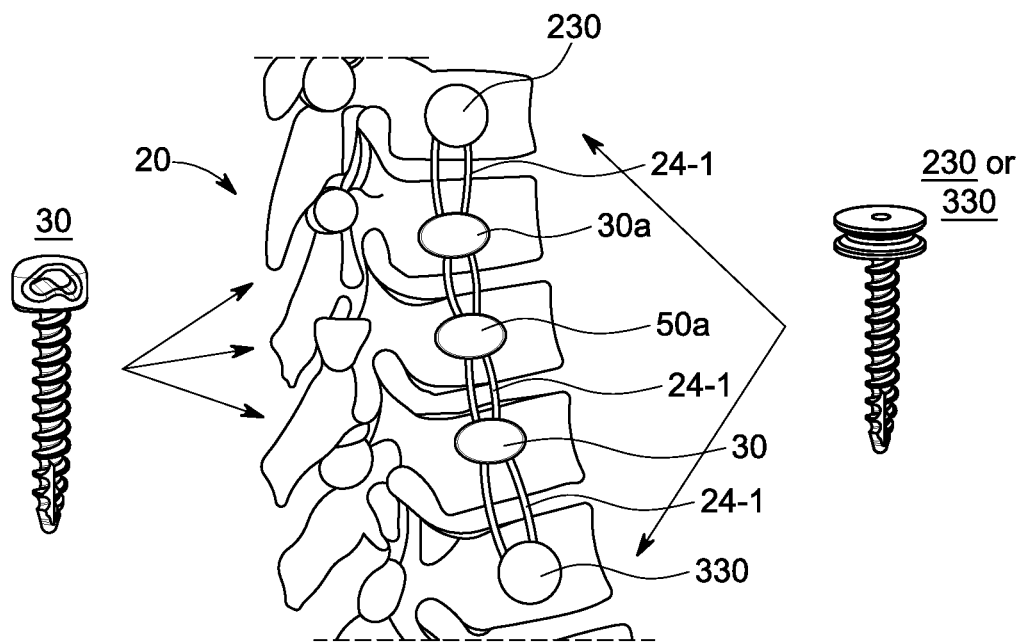
FIG. 36A is a schematic representation of an arrangement of vertebral tethering members and sutures according to another embodiment of the present invention.

FIG. 36A shows a single tethering loop 24-1 extending from a topmost tethering member 230 to a bottommost tethering member 330. The single tethering loop passes through three tethering members 30a, each having a tethering head 50a that provides guidance for the passage therethrough of the single suture loop.

FIGS. 36B-36G show various depictions of tethered anchors arranged in discrete segments. These figures, as well as other figures shown herein, show the tethering together of anchors with a loop of tethering material. In some embodiments, these loops are prepared by manipulating a loose, free piece of tether (with 2 free ends) into a loop. Non-limiting examples of such loops include loops with no remaining free ends; loops in which both free ends remain, after splicing; a single loop with 1 fixed free end extending from the loop; and a single loop in which 1 free end extends from a joint or splice that permits a pulling on the free end, with a subsequent change in the dimension of the loop. It will be understood by those of ordinary skill in the art that the splicing can be accomplished in any manner, including: splicing; use of knots; a single attachment crimping each end together; separate crimped attachments, one for each end, with the crimped attachments being attached together; mechanical joints; fusing, such as by heat or ultrasonics; adhesives; or any other manner.

FIG. 36B shows a portion of tether 24 having 2 free ends 24a and 24b. FIG. 36C shows tether 24 with the free ends spliced together to form an endless loop. FIG. 36D shows the loop 24 of FIG. 36C is attached to a pair of tethering anchors X 30c. In some embodiments, the loop 24 is spliced in a manner that the loop has a fixed size. Therefore, if this loop is attached to a pair of tethering anchors, the loop of tether will be in tension if there is relative movement of the 2 anchors, such that there is an attempt for the anchors to spread apart. As shown in FIG. 36D, the anchors will spread apart commensurate with the fixed geometry of the loop, placing the loop in tension, and further increasing that amount of tension if further separation is attempted.

FIG. 36E shows the portion of tether 24 of FIG. 36B with one of the free ends spliced to an intermediate portion of the tether in a way that creates an adjustable loop. The size of the loop in FIG. 36E can be changed by pulling on the remaining free end. In some embodiments, this change in length is a one-way change in length, such that the configuration of the spliced connection prevents subsequent enlargement of the loop. As examples, the remaining free end 24a may be pulled through a crimp-type attachment until the desired tension is achieved, at which point the crimp is tightened or deformed so as to lock the free end and lock the configuration of the loop. Still further, one-way attachments similar to those used in electronics (such as cable ties or zip ties) can be used, in which the free end is not fixed to the loop, but after pulling and tensioning of the loop, is unable to move backwards through the one-way joint. FIG. 36F shows the loop of FIG. 36E coupled to a pair of tethering anchors spaced apart by a first distance.

FIG. 36G shows the assembly of FIG. 36F after the free end has been pulled so as to create sufficient tension in the tether and draw the 2 anchors together. The resultant configuration shows the 2 anchors spaced apart by a second distance that is less than the distance shown in FIG. 36F. The tension in the loop 24 of FIG. 36G would be proportional to the amount of resistance encountered in changing the spacing of the 2 anchors from the first, greater distance to the second, lesser distance. Such changing of the relative spacing could be a result of movement of the 2 vertebrae as the patient moves; growth of the patient; or tensioning of the loop by the surgeon.

Figure 37:
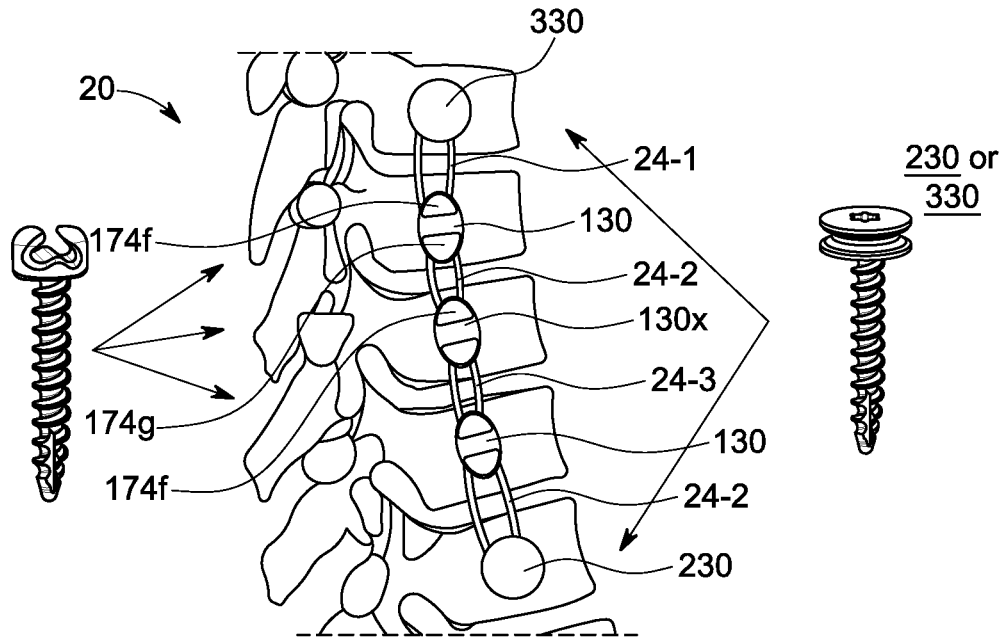
FIG. 37 is a schematic representation of an arrangement of vertebral tethering members and sutures according to another embodiment of the present invention.

Referring to FIG. 37, a spine 20 has implanted within it a plurality of tethering members X30, each of which is interconnected by separate tethers to adjacent tethering members. A first suture loop 24-1 passes around the peripheral groove 364 of a member 330, and then to a first post 174f of the member 130 attached to the adjacent vertebrae. A second suturing loop 24-2 interconnects the other securement post 174g to a tethering post 174f secured to an adjacent vertebrae. This pattern continues through several adjacent vertebrae.

It is further understood that the present invention also contemplates combining in one implantation a mixture of looping members 230 or 330, with both guiding members 30 as well as hitching members 130. For example, in the implantation constructions shown in FIG. 34, the centralmost hitching member 130x could be replaced with a guiding member 30x, such that the loop 24-2 extends through the guiding member 130, and is then linked to a post of the next adjacent hitching member 130. In such a construction, the vertebrae to which guiding member 30x is attached would be somewhat freer to establish its own position between the adjacent vertebrae.

Figure 38:
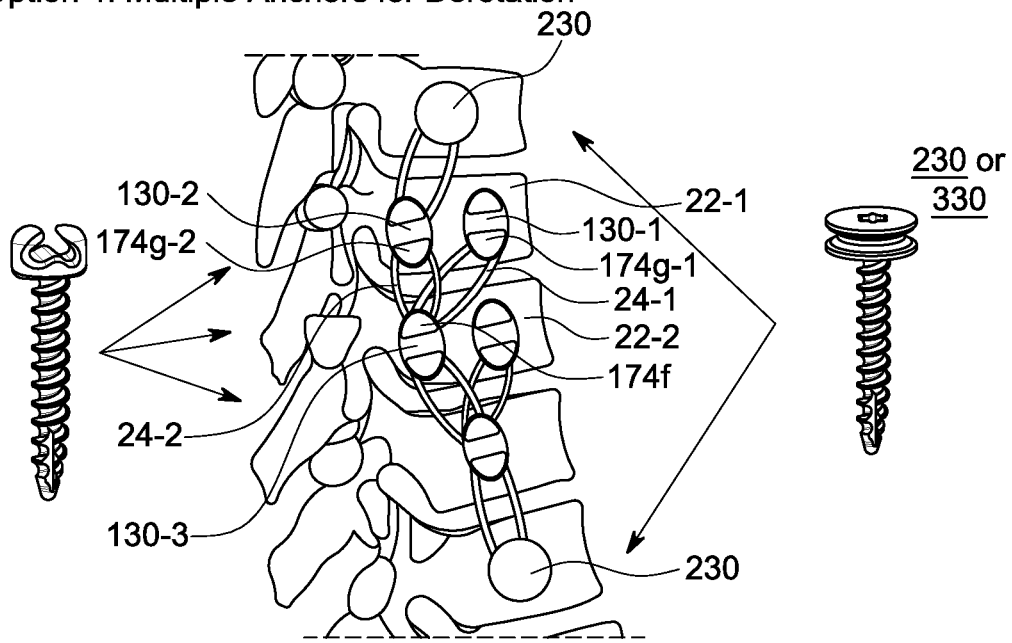
FIG. 38 is a schematic representation of an arrangement of vertebral tethering members and sutures according to another embodiment of the present invention.
Figure 39:
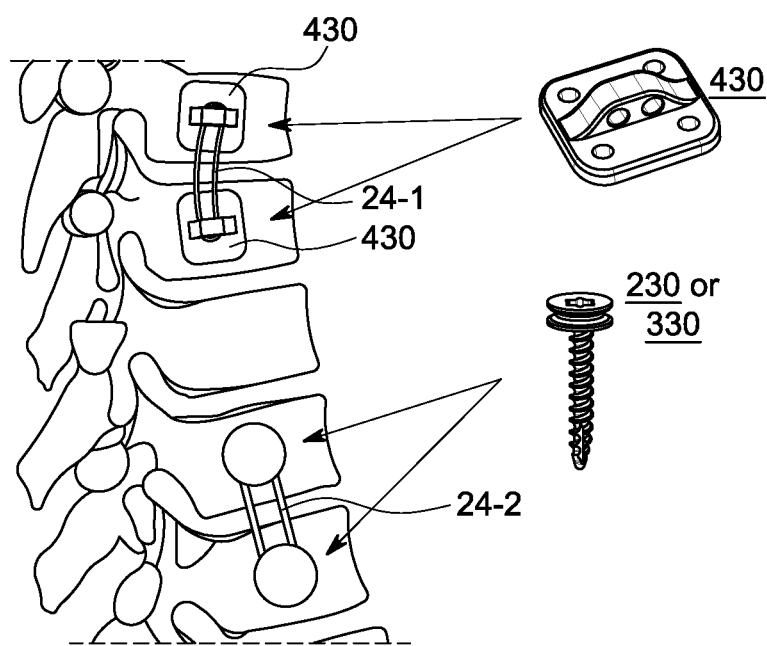
FIG. 39 is a schematic representation of an arrangement of vertebral tethering members and sutures according to another embodiment of the present invention.
Figure 40:
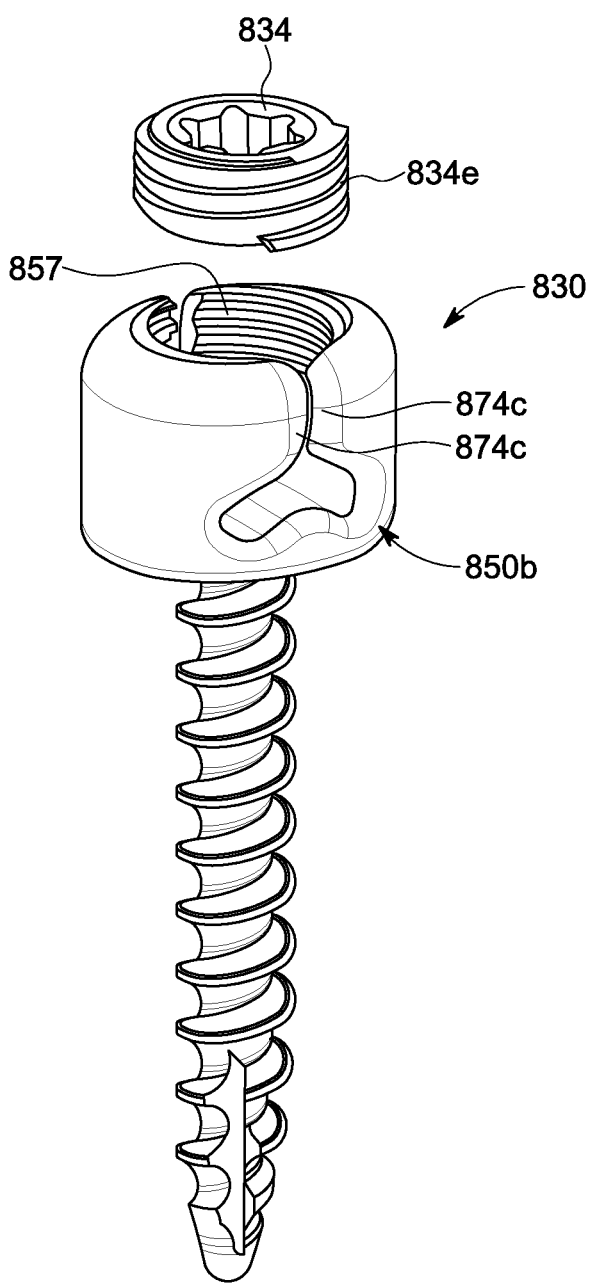
FIG. 40 is a side, top perspective CAD surface representation of a vertebral tethering member according to yet another embodiment of the present invention, shown exploded.
Figure 41:
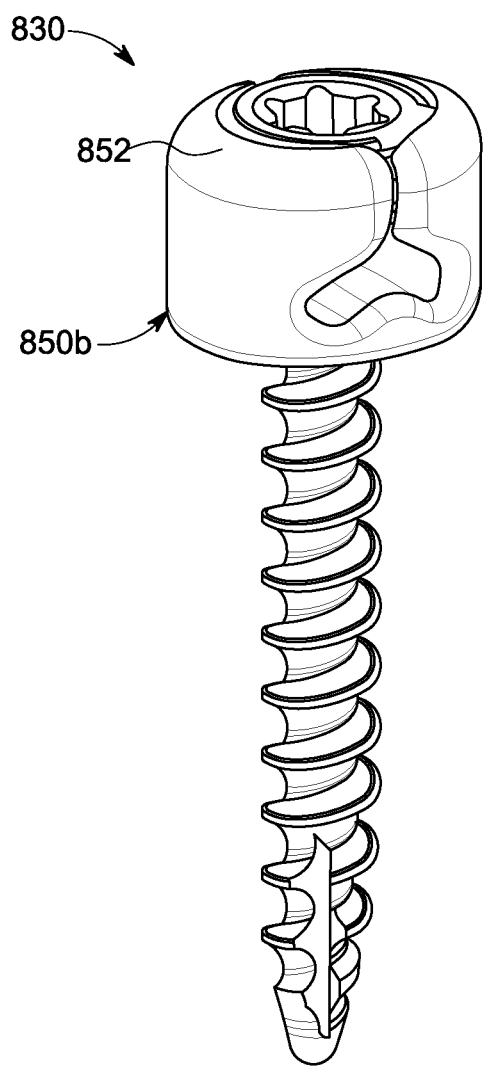
FIG. 41 shows an assembled view of the apparatus of FIG. 40, shown assembled.

Referring to FIG. 38, a pair of vertebral tethering members 130-1 and 130-2 have been secured to a single vertebrae. A third tethering member 130-3 has been secured to an adjacent vertebrae. A common securement post 174f is connected by two suture loops 24-1 and 24-2 to the suturing post 174g-1 and 174g-2 of corresponding members 130-1 and 130-2. In this manner, the lateral offset between members 130-2 and 130-1 can apply a rotational torque of vertebrae 22-1 relative to vertebrae 22-2.

FIGS. 40-71 pertain to still further embodiments 8XX, 9XX, 10XX, and 11XX. Persons of ordinary skill will understand that these embodiments can include various of the features previously shown and described for embodiments XX, 1XX, 2XX, 3XX, 4XX, 5XX, 6XX, and 7XX, without the need to state each and every one of these many combinations.

FIGS. 40-46 show various views of a vertebral tethering member 830 according to another embodiment of the present invention. Member 830 includes various design aspects found in either of tethering members 30 or 130 as previously discussed.

Tethering member 830 includes a tethering head X50b and means 40 for connecting the head to a vertebrae. Tethering head 850b includes within it an upside down, enclosed V-shaped passageway 854. In the embodiment shown, connecting means 840 is an anchoring screw 844 that includes a plurality of threads 844c on a shaft 844a. Connecting means 840 extends from a neck 842 that attaches to the underside of head 850b to a tip 44b that is adapted and configured to be inserted into a hole in the vertebrae. The necks X42 shown herein preferably include increased cross sectional areas proximate to this attachment, so as to manage the distribution of stresses and forces transitioning between the head and the connection means.

Tethering head 850*b* includes within it a passageway 854. In some embodiments, this passageway 854 includes separated first and second passageways 854*e* and *f*, preferably arranged in a V-shape. Although as shown in FIGS. 6 and 7, the V-shape is "upside down" (with the vertex of the V being proximate to the top surface 852*f* of the head), yet other embodiments include passageways separated in yet other configurations, including V-shapes with the vertex pointed downward, FIG. 8 shapes, barbell shapes, and the like. Still further, yet other embodiments include single passageways of rounded, smooth cross sectional shapes, including circular and elliptical cross sectional shapes, including shapes that are not separated into multiple passageways. Still further, although what has been shown and described includes tethering heads having two passageways, it is further contemplated in yet other embodiments that the tethering heads can include three or more smoothly separated passageways, including separation features having cross sectional shapes resembling a smooth, rounded upside down W-shape.

Vertebral tethering member 830 includes a head 850*b* that can provide either the "hitching" or looping-connection shown in head 150*b* as well as the guiding support of head 50*a* of member 30. Comparing FIGS. 42 and 2, it can be seen that the head 850*b* includes a passageway 854 that looks similar to the passageway 154, except that tethering member 830 includes a suture capturing member 834 that closes the slot or opening 873.

Referring to FIG. 43, it can be seen that in one embodiments the capturing member 834 is a setscrew that includes a plurality of external threads 834*e* that are threadably received within the connection feature 857. Comparing FIGS. 40 and 42, it can be seen that a loop of tether can be placed within the V-groove 854, so as to mount one or more suture loops in a hitching manner around a securement post 874, in a manner as previously described relative to tethering member 130. Placement of the capturing member 834 within the slot 873 subsequently closes the slot, preventing escape of any of the loops being hitched to or placed within member 830. However, the securement of capturing member 834 within slide 873 preferably does not compress the flexible tether, and preferably further does not contact the flexible tether. Therefore, even with setscrew 834 firmly coupled to threads 834*e*, the pathway 854 is unconstrained, and the flexible tether can move freely within passageway 854.

Alternatively, one or more suture paths can be guided within passageway 854 in a manner as previously described for tethering member 30. However, because tethering head 850*b* incorporates an opening 873 that extends entirely across the top surface 852 and into passageway 854, the guided sutures can be placed within passageway 854 from above the head and through slot 873. This is in contrast to member 30 in which the sutures are preferably guided through passageway 54 by entering the passageway on one lateral side of the head and bringing the suture out of the opposite side of the lateral head.

By use of a suture capturing member 834 to securely close slot 873, a tethering member 830 can provide guidance or hitching of suture material, similar to members 30 and 130, respectively, described previously. The suture can be a simple pass through, in which the suture approaches slot 854 in a manner at least somewhat parallel to the pathway or the slot, or alternatively can approach the pathway 854 orthogonally for hitching-type securement. It is also understood that the securement post or head lateral sides 874 can be of the configuration discussed with regards to FIG. 17, except that the opposing surfaces of the overhangs 874*c* are preferably adapted and configured for securement to the capturing member, such as the threads shown in FIGS. 43 and 44.

Other similarities between member 830 and members 30 and 130 can be seen, such as the passageways 854*e* and 854*f* on opposite sides of head 850*b*, with the passageways being angled in an approximate V-shape 856*b*, with the included angle 856*c* of the V-shape being preferably greater than about ninety degrees. Further in comparison of FIGS. 13 and 6, it can be seen that the floor 856 includes a convex feature 856*a* that roughly parallels the V-shape with a smooth ridge 856*d*.

FIGS. 47-55 show various views of a vertebral tethering member 930 according to one embodiment of the present invention. Tethering member 930 includes a tethering head 950*a* and means 40 for connecting the head to a vertebrae. Tethering head 50*a* includes within it a pair of separated passageways 954. In the embodiment shown, connecting means 40 is a separable anchoring screw 44 that includes a plurality of threads 944*c* on a shaft 44*a*. Connecting means 40 extends from a head 947 to a tip 944*b* that is adapted and configured to be inserted into a hole in the vertebrae.

Figure 48:
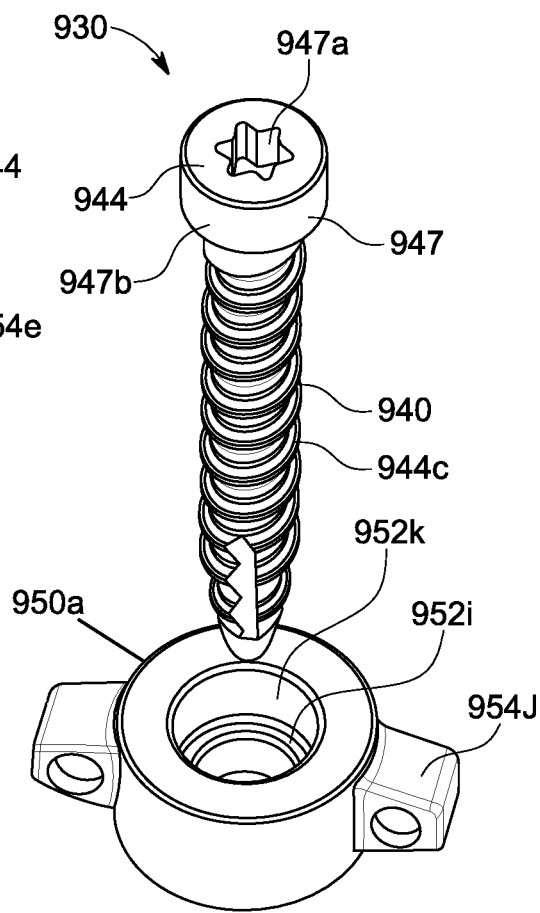
FIG. 48 shows an assembled view of the apparatus of FIG. 40, shown exploded.
Figure 49:
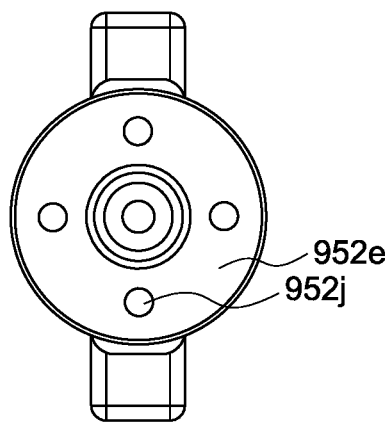
FIG. 49 is a bottom plan view of the apparatus of FIG. 47.

Vertebral tethering member 930 in some embodiments is an assembly of a tethering head 950*a* that is separate from the anchoring means 940. Referring to FIG. 48, it can be seen that connecting means 940 includes a head 947 attached to a shaft 944*a* that has a plurality of bone-engaging threads 944*c*. Head 947 preferably incorporates a driving feature 947*a* that receives a tool operated by the user, through which a torque can be applied to connecting means 940.

Figures 53, 54, 55:
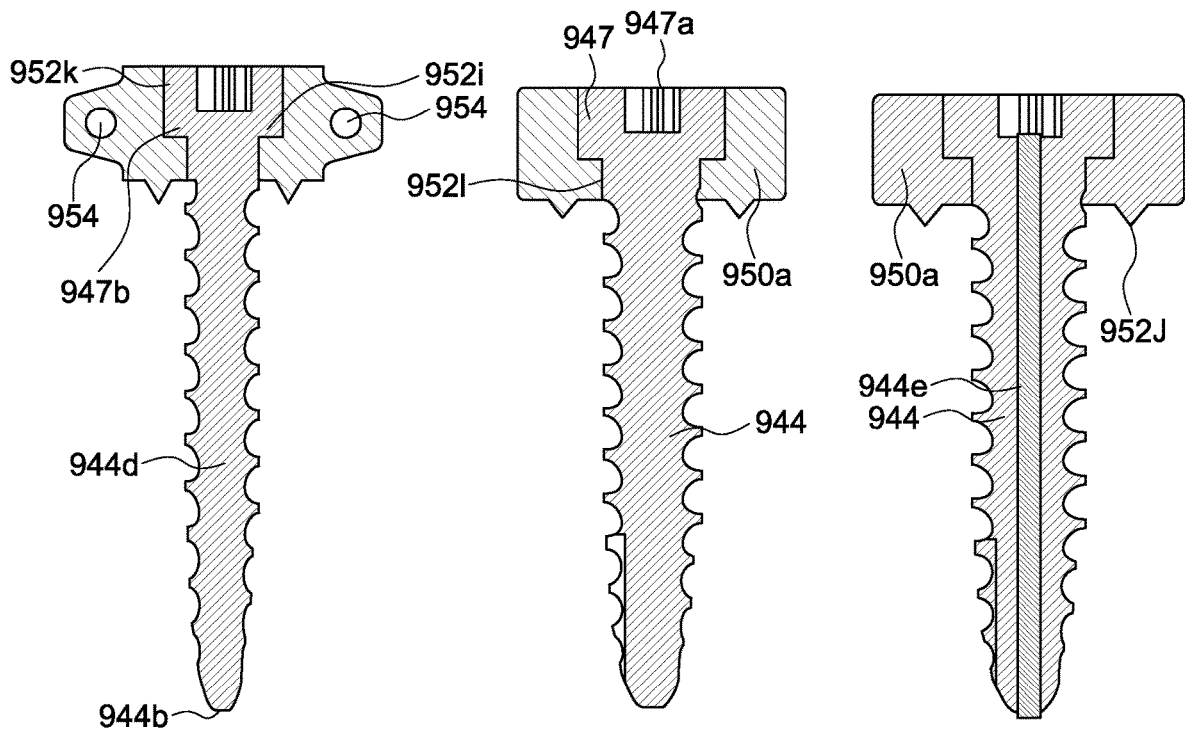
FIG. 53 is a cross sectional view of the apparatus of FIG. 52, with a cross section parallel to the plane of the figure.
FIG. 54 is a cross sectional view of the apparatus of FIG. 51, with a cross section parallel to the plane of the figure.
FIG. 55 is a cross sectional representation of the apparatus as shown in FIG. 53, expect modified to include a central cannula.

Referring to FIGS. 48, 53, and 54, it can be seen that head 950*a* includes a through aperture that receives therein the head and shaft of connecting means 940. The through aperture includes a first, larger cylindrical well 952*k* that slidably receives the outer surface of head 947. A second, smaller diameter aperture 952*l* that extends the rest of the way through the bottom surface of head 950*a*. Preferably, either one of these cylindrical surfaces 952*k* or 952*l* are close-fitting to the corresponding outer diameter of anchoring means 940, with the other of cylindrical well 952*k* or aperture 952*l* being a clearance fit.

Separating the two inner diameters is a compression surface 952*i* that abuts against a compression surface 947*b* of head 947. When torque is applied to connecting means 940, the two compression surfaces come into contact, and connecting means 940 pulls head 950*a* into contact with the vertebra.

With this separation of the anchoring means from the tethering head, it is possible for the user to provide any angular orientation to the tethering head, with such angular orientation being maintained while connecting means 940 is rotated and tightened. In some embodiments, the frictional interface between compression surfaces 952*i* and 947*b* may be coated to provide desirable characteristics. As one example, one or more of the surfaces can be coated with a low friction substance.

In yet another embodiment shown in FIG. 55, the connecting means 940 can include a cannula adapted and configured for a surgical tool such as a guide wire or guide pin. In some embodiments, the installation of tethering member 930 may be facilitated by the use of one or more tools to provide accurate location of member 930. As one example, the surgeon can determine where best to locate the separate tethering head 950*a*. Once the location is established, a tool (not shown) having a cross sectional shape similar to that of the head and neck of connecting means 940 can be placed within the well 952*k*. A small central hole within the tool then provides guidance for another tool, such as a drill or a pin, which can be placed through the central hole of the tool. The surgeon can use this tool to accurately locate the hole, and then using the same tool, or another different tool, provide guidance for a drill that creates the hole for coupling to the threads 944c.

Figure 47:
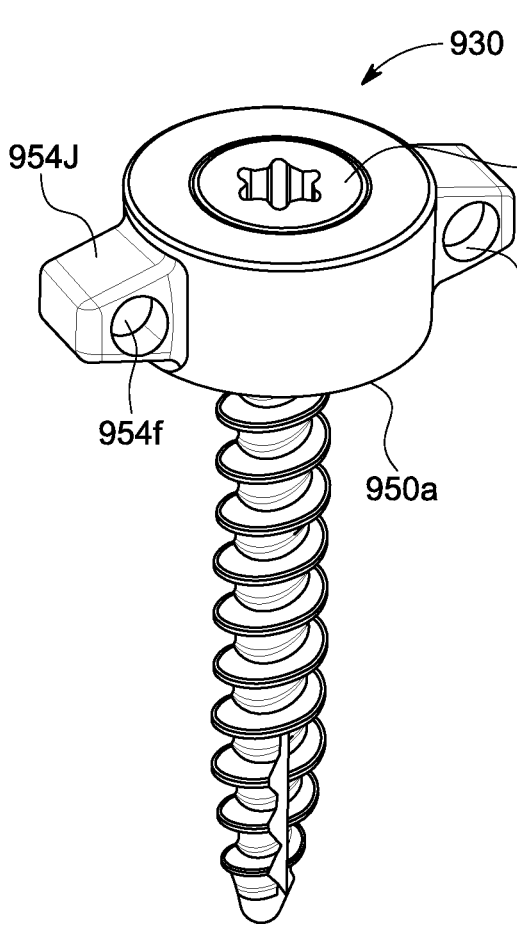
FIG. 47 is a side, top perspective CAD surface representation of a vertebral tethering member according to yet another embodiment of the present invention, shown assembled.
Figure 50:
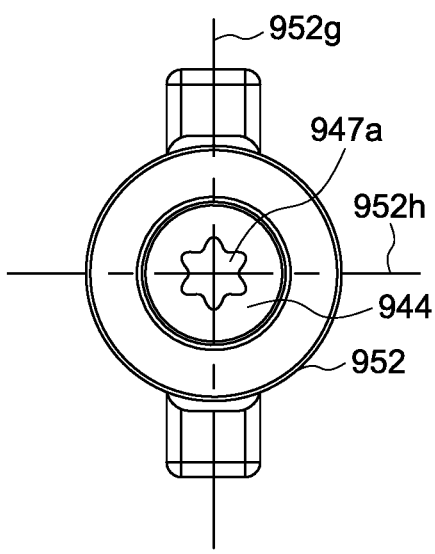
FIG. 50 is a top plan view of the apparatus of FIG. 47.
Figures 51, 52:
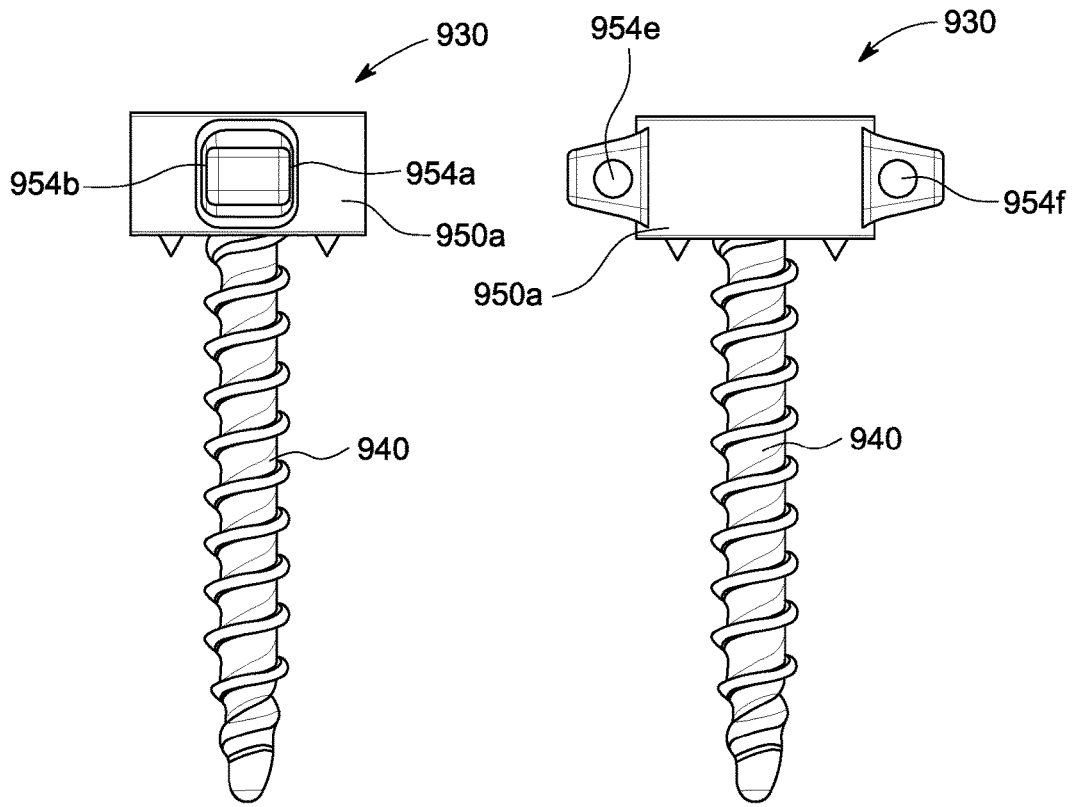
FIG. 51 is a side elevational view of the apparatus of FIG. 47.
FIG. 52 is a frontal view of the apparatus of FIG. 47.

Referring to FIGS. 47 and 50, it can be seen that head 950a has a generally cylindrical planform shape 952, with a pair of ears 954j extending from opposite sides. Each of the ears 954j contain within them the corresponding passageway 954e or 954f, through which the suture material is passed. As shown in these figures, the ears 954j are located on opposite sides of the planform shape 952, and as seen in FIG. 50, the tethering head 958 is symmetrical about planes 952g and 952h.

However, the present invention also contemplates those embodiments in which the outwardly extending ears 954j are not located on opposite sides, but instead have a relative angular orientation that is other than 180 degrees of separation. Further, yet other embodiments contemplate heads 950a that have more than two outwardly extending ears 954j, such as embodiments having three or more equally (or non-equally) spaced ears. Still further, yet other embodiments contemplate head planform shapes 952 in which the passageways 954f and 954g are at least partly located and integrated within the outer diameter of the circular planform, and further those embodiments in which the passages 954e and 954f are located entirely within the cylindrical planform shape.

Passageways 954e and 954f are adapted and configured to permit the unrestrained passage therethrough of the 2 or more strands of a single continuous (or endless) loop of tethering material. The end of the loop and the strands of the loop are provided to the entrance 954a of the passageways, and leave the passageway through exit 954b (referring to FIG. 51). It is understood that the terms entrance and exit are used for convenience, and that the loop and strands can be entered or exited through either side. Referring to FIG. 9, it can be seen that the shape 952 of head 950 is symmetric about the two planes 952g and 952h as shown. However, other embodiments of the present invention contemplate shapes of tethering heads that have only a single plane of symmetry, or no symmetry at all. In such embodiments, one of the entrance and exit may have one or more distinctly different features than the other of the entrance or exit.

FIGS. 56-61 show various views of a vertebral tethering member 1030 according to another embodiment of the present invention. Tethering member 1030 includes a separate tethering head X50c and separate means 40 for connecting the head to a vertebrae. Tethering head 1050c includes one or more peripheral grooves 1064 extending around the planform shape 1052 of the head. In the embodiment shown, connecting means 1040 is an anchoring screw 1044 that includes a plurality of threads 1044c on a shaft 1044a.

In some embodiments, a tethering member 1030 comprises a two-piece assembly of separate components, similar to that discussed with regards to tethering member 930. Referring to FIG. 57, it can be seen that connecting means 1040 includes a head 1047 attached to a shaft 1044a that has a plurality of bone-engaging threads 1044c. Head 1047 preferably incorporates a driving feature 1047a that receives a tool operated by the user, through which a torque can be applied to connecting means 1040.

Figures 60, 61:
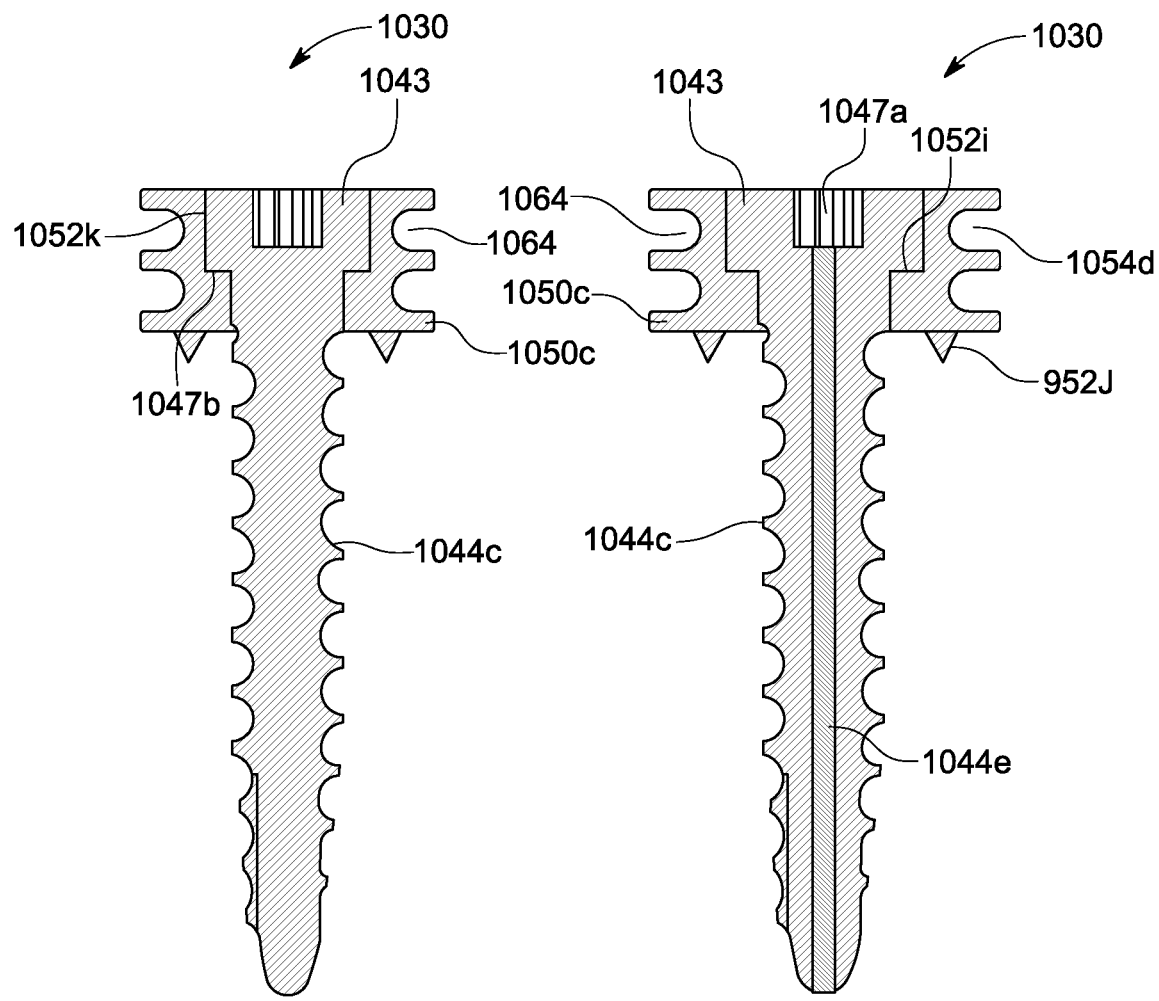
FIG. 60 is a cross sectional view of a side elevational representation of the apparatus of FIG. 56, with the cross section taken through the centerline.
FIG. 61 shows a modification of the apparatus of FIG. 60 to include a central cannula.

Referring to FIGS. 57 and 60, it can be seen that head 1050a includes a through aperture that receives therein the head and shaft of connecting means 1040. The through aperture includes a first, larger cylindrical well 1052k that slidably receives the outer surface of head 1047. A second, smaller diameter aperture 1052l that extends the rest of the way through the bottom surface of head 1050a. Preferably, either one of these cylindrical surfaces 1052k or 1052l are close-fitting to the corresponding outer diameter of anchoring means 1040, with the other of cylindrical well 1052k or aperture 1052l being a clearance fit.

Separating the two inner diameters is a compression surface 1052i that abuts against a compression surface 1047b of head 1047. When torque is applied to connecting means 1040, the two compression surfaces come into contact, and connecting means 1040 pulls head 1050a into contact with the vertebra.

With this separation of the anchoring means from the tethering head, it is possible for the user to provide any angular orientation to the tethering head, with such angular orientation being maintained while connecting means 1040 is rotated and tightened. In some embodiments, the frictional interface between compression surfaces 1052i and 1047b may be coated to provide desirable characteristics. As one example, one or more of the surfaces can be coated with a low friction substance.

In yet another embodiment shown in FIG. 61, the connecting means 1040 can include a cannula adapted and configured for a surgical tool such as a guide wire or guide pin. In some embodiments, the installation of tethering member 1030 may be facilitated by the use of one or more tools to provide accurate location of member 1030. As one example, the surgeon can determine where best to locate the separate tethering head 1050a. Once the location is established, a tool (not shown) having a cross sectional shape similar to that of the head and neck of connecting means 1040 can be placed within the well 1052k. A small central hole within the tool then provides guidance for another tool, such as a drill or a pin, which can be placed through the central hole of the tool. The surgeon can use this tool to accurately locate the hole, and then using the same tool, or another different tool, provide guidance for a drill that creates the hole for coupling to the threads 1044c.

Vertebral tethering member 1030 includes a tethering head 1050c adapted and configured for looping connection to a flexible tether or suture. Referring to FIG. 56, it can be seen that a tethering head X50c preferably includes at least one peripheral groove 1064 that extends around the smooth outer surface X52d of head X50c. In one embodiment, this groove is recessed into the periphery, with the inner wall 1054d of the groove being smoothly contoured and rounded for minimal abrasion with a suture loop placed within the groove. In one embodiment, as shown in FIG. 56, the inner wall 1054d has a semi-circular shape, although other embodiments of the present invention contemplate smoothly contoured and rounded walls of any shape, including walls having elliptical cross sections and parabolic cross sections as examples.

Preferably, the groove includes a top and bottom pair of walls 1054h and 1054i, respectively that, combined with the innermost wall 1054d, form the suture loop passageway 1054. Preferably and similar to the passageway of heads 250c and 350c, this passageway has a width 1064c greater than the unstressed diameter of the suture material, as well as a depth 1064d greater than the unstressed diameter of the suture material. By having groove dimensions greater than the unstressed diameter, the physician will easily wrap the unstressed loop around and into passageway 1054, and preferably without the need to push or force the suture material into the groove. However, yet other embodiments of the present invention contemplate a groove 1064c in which the unstressed material fits tightly and securely within the groove.

The top and bottom surfaces 1054h and 1054i, combined with the depth 1064d of passageway 1054, result in the implanted suture remaining securely within the groove, and not escaping the groove even if the tension on the suture is slightly relieved. The overhang of the top and bottom walls 1054h and 1054i also provide protection to the suture loop within groove 1054 from abrasion from other nearby features.

FIGS. 56, 60, and 61 show that in some embodiments head 1050c includes a pair of spaced apart grooves, similar to that shown and described for tethering member 330. Preferably, these grooves are spaced apart vertically from the underside, bone contacting surface 1052e. Member 1030 permits a single tethering member to apply tension in two different directions, each direction being provided by a different suture loop.

FIGS. 58 and 59 show top and bottom views, respectively, of tethering member 1030. Tethering member 1030 includes a central driving feature 1052c for applying torque to the tethering member. Further, both tethering members permit a variety of suture approach directions 26c, similar to that shown with FIG. 21. The strands of the suture can exit radially outwardly in any direction. Still further, a strand (and not a complete loop) can be wrapped part way around the groove, and depart (or approach) a head X50c tangentially to the groove, as expressed by the arrow 26c of FIG. 21 shown at about the three o'clock position. It is understood that the tethering member 1030, as discussed above, is adapted and configured to provide connection to two different suture loops, each approaching in two different directions, and in any of the manners discussed with regard to tether member 230.

FIGS. 62-71 show various views of a vertebral tethering member 1130 according to another embodiment of the present invention. Tethering member 1130 includes a tethering head X50b and means 40 for connecting the head to a vertebrae. Similar to members 930 and 1030 previously discussed, tethering member 1130 is preferably an assembly of two separate components, a connecting means 1140 and a tethering head 1150b.

Figures 62, 63:
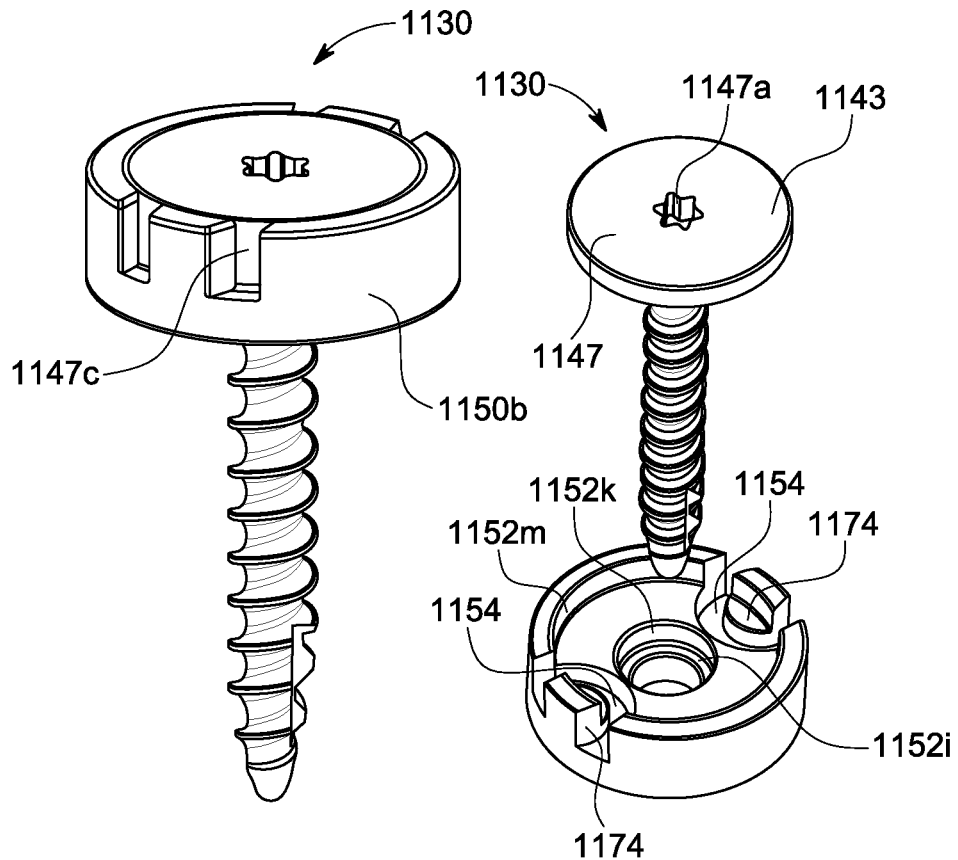
FIG. 62 is a side, top perspective CAD surface representation of a vertebral tethering member according to yet another embodiment of the present invention, shown assembled.
FIG. 63 shows an assembled view of the apparatus of FIG. 40, shown exploded.

Referring to FIGS. 63 and 65, it can be seen that the head 1147 preferably includes three distinct outer diameters of decreasing size. The smallest diameter is adapted and configured to be received within a through aperture of head 1150b. A larger, intermediate outer diameter is received within a well 1152k of the tethering head, and preferably provides location of head 1147 relative to head 1150b (the larger and smaller outer diameters being clearance diameters creating a small circumferential gap). Referring to FIG. 65, this intermediate diameter of the head 1147 preferably includes a compression surface 1147b that, after assembly, presses against an opposite compression surface 1152i of head 1150b. The coupling and reception of the intermediate and smallest diameters of head 1147 within head 1150b is similar to the manner described previously for tethering members 930 and 1030.

Head 1147 includes a largest diameter having an undersurface 1147c that provides the top enclosure for passageways 1154e and 1154f. Referring to FIGS. 65 and 66, it can be seen that three sides of the passageways 1154 are preferably formed within head 1150b. A loop of suture material can be placed around either of the securement posts 1174f or 1174g, and preferably placed within the semi-circular passageways 1154f and 1154e. Once the loops are placed within these open passageways 1154, the securement of connecting means 1140 to the vertebrae places the underside 1147c of the head on top of the passageways, thus completing the enclosure of the passageways.

Figure 64:
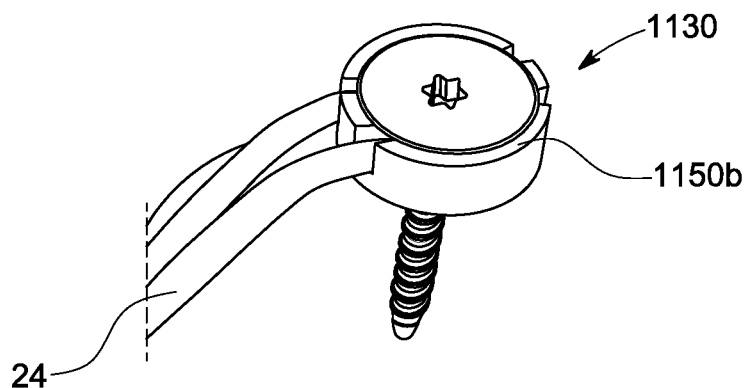
FIG. 64 is a photographic representation of the apparatus of FIG. 62 shown with a portion of tether, hitched to the tethering head.
Figures 70, 71:
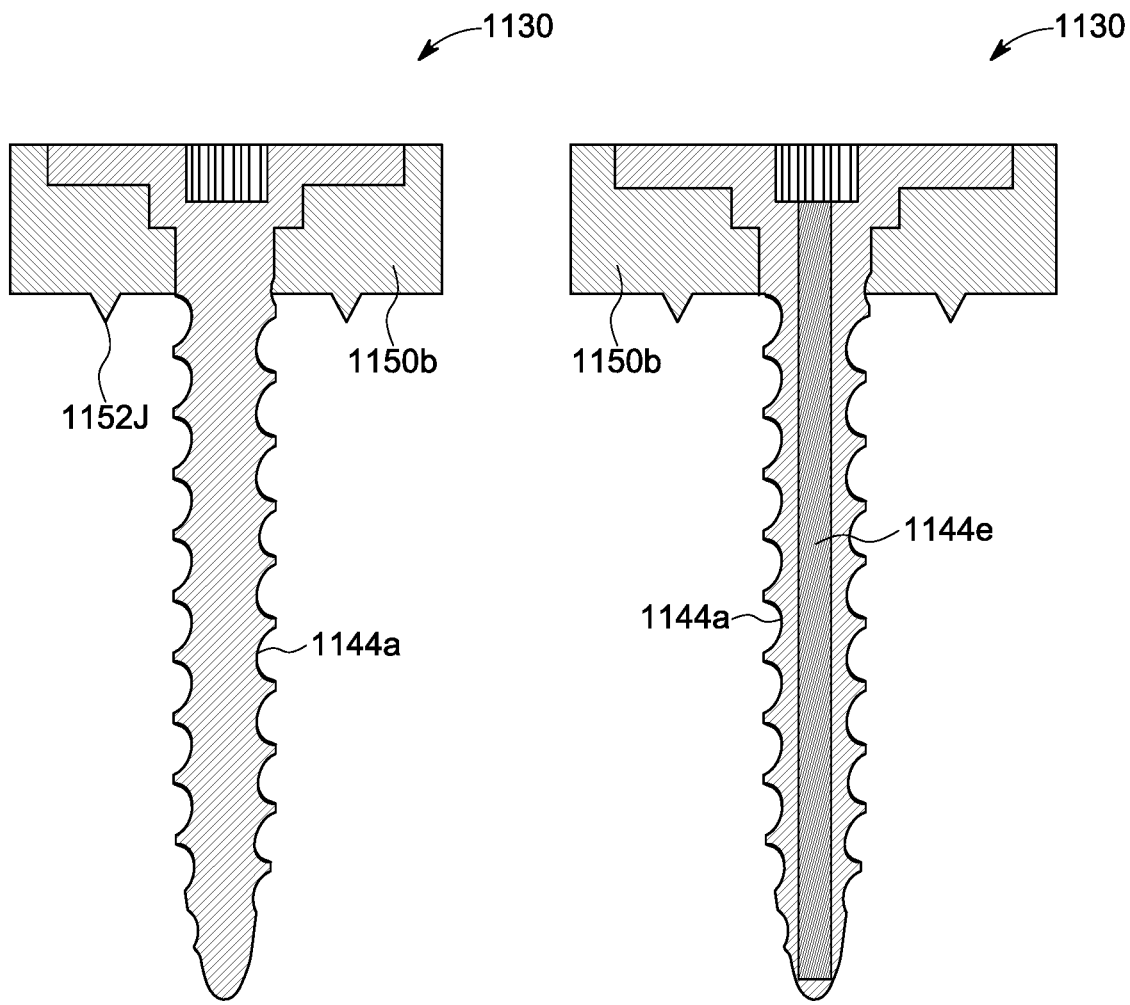
FIG. 70 is a side elevational cross sectional view of the apparatus of FIG. 66, with a cross section taken through the centerline and perpendicular to the viewing plane.
FIG. 71 is a cross sectional representation of an apparatus similar to that shown in FIG. 70, except having a central cannula.

As seen in FIG. 64, the tether material is looped or hitched around the passageway 1154, extending out of the passageway. Preferably, the securement of connecting means 40 to the bone does not pinch or compress or otherwise prevent sliding movement of the tether material 24. Referring to FIG. 71, a variation of tethering member 1130 includes a connecting means 40 that has a central cannula 1144e that facilitates use of a separate tool (not shown) for accurate location of tethering member 1130.

Various aspects of different embodiments of the present invention are expressed in paragraphs X1, X2, X3, X4, X5, X6, X7, X8, X9, X10, X11, and X12 as follows:

X1. Another aspect of the present invention pertains to a member for connection to a bone. The member preferably includes a head. The member preferably includes means for connecting the head to a bone; and means for coupling the head to a flexible material, wherein the connecting means and the head are separate devices.

X2. Yet another aspect of the present invention pertains to a member for tethered connection to a bone. The member preferably includes a bone connecting member, and a tethering head attached to the bone connecting member, the tethering head including at least one passageway extending in the head; the passageway being adapted and configured to accept therein a flexible tether, the tethering head including a slot extending across the top surface of the tethering head, the slot providing through access to the passageway, the passageway having internal threads. The member preferably includes a threaded member adapted and configured to be threadably received within the slot.

X3. Still another aspect of the present invention pertains to a member for tethered connection to a bone. The member preferably includes a bone connecting member and a tethering head independent of the bone connecting member, the tethering head including a bone contacting surface; the tethering head being adapted and configured for joining to the bone by the bone connecting member; such that connection of the bone connecting member to a bone places the bone contacting surface in contact with the bone.

X4. Yet another aspect of the present invention pertains to a member for tethered connection to a bone. The member preferably includes a bone connecting member and, and a tethering head disconnectable from the bone connecting member, the head including being adapted and configured to accept therein a flexible tether, the passageway being externally accessible. The member preferably includes a cover adapted and configured to cover the passageway and the external access X5. One aspect of the present invention pertains to a member for connection to a bone. The member preferably includes a head and means for connecting the head to a bone. The member preferably includes means for coupling the head to a flexible material.

X6. Another aspect of the present invention pertains to a member for tethered connection to a bone. The member preferably includes a bone connecting member adapted and configured for connection with a bone. The member preferably includes a head attached to the bone connecting member, the head at least one passageway extending across the head; the passageway being adapted and configured to accept therein a corresponding tether, the passageway having an entrance on one side of the head and an exit on the opposing side of the head, the passageway being enclosed from the top surface of the head.

X7. Yet another aspect of the present invention pertains to a member for tethered connection to a bone. The member preferably includes a bone connecting member adapted and configured for connection with a bone. The member preferably includes a head attached to the bone connecting member, the head including at least one securement post each adapted and configured for connection to a loop of a flexible tether, the post including a groove sized to accept therein a tether loop.

X8. Still another aspect of the present invention pertains to a member for tethered connection to a bone. The member preferably includes a bone connecting member adapted and configured for connection with a bone. The member preferably includes a head attached to the bone connecting member, the head including at least one peripheral groove adapted and configured for connection to a separate loop of flexible tether, the head having a top surface furthest away from the vertebrae, wherein the at least one peripheral groove is between the top surface and the bone.

X9. Another aspect of the present invention pertains to a method for tethering of vertebrae. The method preferably includes attaching a first tethering head to a first bone. The method preferably includes attaching a second tethering head to the first bone spaced apart from the first tethering head. The method preferably includes attaching a third tethering head to a second bone. The method preferably includes looping one end of a first flexible tether in a first groove in the first tethering head. The method preferably includes looping one end of a second flexible tether in a second groove in the second tethering head. The method preferably includes connecting the first bone to the second bone by looping the other end of the first flexible tether within a groove in the third tethering head, and connecting the first bone to the second bone by looping the other end of the second flexible tether within a groove in the third tethering head.

X10. Yet another aspect of the present invention pertains to a method for tethering of vertebrae. The method preferably includes attaching a first tethering head to a first bone. The method preferably includes attaching a second tethering head to a second bone. The method preferably includes looping a flexible tether in a first groove extending around the periphery of the first tethering head. The method preferably pertains to extending the looped tether from the first tethering head to the second tethering head; and passing the extension of the looped tether though an aperture in the second tethering head.

X11. Still another aspect of the present invention pertains to a device for making a flexible connection between bones. The device preferably includes a bone connecting member adapted and configured for connection with a bone, the bone connecting member including an alignment feature. The device preferably includes a separable receiver for a flexible connector, the receiver having a body including a protrusion with a passageway for a flexible connector and including a first central aperture adapted and configured to receive therein the alignment feature. The device preferably includes a central pocket that couples to the receiver, the central pocket including a lateral aperture that permits placement therethrough of the protrusion.

X12. Another aspect of the present invention pertains to a member for making a flexible connection between bones. The member preferably includes a connecting member having a first aligning element. The member preferably includes a first separable receiver for a flexible connector, the first receiver having a body including a first protrusion and provisions for a flexible connector. The member preferably includes a head having a pocket that receives therein the first receiver, the pocket including a first lateral aperture that permits placement therethrough of the first protrusion, the head including a second aligning element adapted and configured to couple with the first aligning element, wherein placement of the first receiver within the central pocket permits alignment of the first aligning element with the second aligning element to capture the first and second separable receivers between the head and the connecting member.

Yet other embodiments pertain to any of the previous statements X1, X2, X3, X4, X5, X6, X7, X8, X9, X10, X11, or X12, which are combined with one or more of the following other aspects. It is also understood that any of the aforementioned X paragraphs include listings of individual features that can be combined with individual features of other X paragraphs.

Wherein said coupling means includes a groove extending around the periphery of said head, the groove being adapted and configured to contain the flexible material.

Wherein the flexible member has a diameter, and the width of the groove is greater than the diameter, and the depth of the groove is greater than the diameter.

Wherein said coupling means includes a pair of separated grooves each extending around the periphery of said head, each groove being adapted and configured to contain the flexible material.

Wherein said shaft has an axis, and each groove is substantially perpendicular to the axis.

Wherein said coupling means includes first and second passageways each extending through the interior of said head, each having an entrance for the flexible material and an exit for the flexible material, each entrance and exit being on opposite sides of said head, each of the passageways being smooth and uninterrupted between the corresponding entrance and exit.

Wherein the first and second passageways have uninterrupted side boundaries.

Wherein a portion of the first and second passageways proximate to the neck of said shaft are smooth and continuous.

Wherein the portion of the first and second passageways does not include a blind hole; or the first and second passageways are open to the top surface of said head; or the first and second passageways are enclosed relative to the top surface of said head.

Wherein said coupling means includes first and second passageways each have opposing lateral walls, each lateral wall extending between a corresponding exit and entrance for that passageway, and each lateral wall transitions to the exterior surface of said head proximate to the respective exit or entrance with a radius of curvature greater than ninety degrees.

Wherein said coupling means includes first and second passageways each having an entrance for the flexible material and an exit for the flexible material, each said passageway extending a length from entrance to exit, said head has a maximum width, a minimum width less than the maximum width, and the length of each passageway is less than the minimum width.

Wherein said coupling means includes first and second passageways each having an entrance for the flexible material and an exit for the flexible material, each said passageway extending a length from entrance to exit, said head has a maximum width, and the length of each passageway is less than the maximum width.

Wherein said coupling means includes means for convexly separating the first passageway from the second passageway.

Wherein said convex separating means includes a smooth bump between the first and second passageways; or said convex separating means includes a smooth ridge between the first and second passageways.

Wherein the top of said head includes an open slot permitting passage of the flexible material into each of the passageways.

Wherein the top of head is closed between passageways, such that a portion of flexible material passing through a passageway cannot be lifted vertically out of the passageway.

Wherein the first and second passageways are substantially parallel.

Wherein the first and second passageways combine in a cross-sectional V-shape with the opened end of the V-shape being directed toward the neck of said shaft.

Wherein said head has a maximum width greater than the outer diameter of the threads; or said head has a width orthogonal to the maximum width that is greater than the outer diameter of the threads but less than the maximum width; or said head has a minimum width orthogonal to the maximum width that is less than the maximum width.

Wherein said shaft, said head, and said coupling means are unitary.

Wherein the outer surfaces of said head are smooth.

Wherein said head has a non-circular outer peripheral shape adapted and configured to receive a driving torque from a driving tool having a complementary inner peripheral shape.

Wherein said head has a distal side adapted and configured for resting on the bone when the anchor is fully inserted into the bone.

Wherein said head has a distal side that is substantially flat

Wherein said connecting means includes a shaft having proximal and distal ends, the distal end including a tip adapted and configured for entry into a hole in a bone, the proximal end including a neck, said shaft including a plurality of threads intermediate of the tip and the neck, the threads being adapted and configured for connection with a vertebrae.

Wherein said connecting means includes a post adapted and configured to connection to a vertebrae; or said connecting means includes an adjustable loop adapted and configured for connection around a vertebrae; said connecting means includes a hook adapted and configured to connection to a vertebrae.

Whether the flexible material is a suture, tether, cord, or wire.

Wherein the flexible material is fabricated from a polymeric compound, or from a metal.

Wherein said head includes smoothly contouring walls defining said first and second passageways, the walls being adapted and configured to permit sliding movement of a tether against the wall without abrasively damaging the tether.

Wherein each said passageway has a smooth elongated cross section shape.

Wherein each first and second cross sectional shape is elongated along a respective first or second axis, and the angle included from the first axis to the second axis is more than about ninety degrees and less than one hundred and twenty degrees.

Wherein each first and second cross sectional shape is elongated along a respective first or second axis, and first and second axes have a V shape with the open side of the V being oriented toward said bone connecting member.

Wherein the apex of the V shape is within said head.

Wherein each said post has a maximum width, said head has a minimum width, and the maximum width is less than the minimum width.

Wherein said coupling means includes first and second passageways each having an entrance for the flexible material and an exit for the flexible material, each said passageway extending a length from entrance to exit, said head has a maximum width, and the length of each passageway is less than the maximum width.

Wherein the top surface of said head includes a central slot having a width sized to permit passage therethrough of the flexible tether.

Wherein said head includes a smoothly contoured convex lower surface that extends between said first and second posts.

Wherein each said post includes smoothly contouring walls defining the respective groove, the walls being adapted and configured to permit sliding movement of a tether against the wall without abrasively damaging the tether.

Wherein said peripheral grooves are substantially parallel to each other.

Wherein said head has a peripheral shape that is rounded, circular, or oblong or elliptical.

Wherein the aperture includes two separated passageways and wherein said passing includes guiding one side of the tether loop within one passageway and guiding the other side of the tether loop within the other passageway.

Which further comprises attaching a third tethering head to a third bone, the second bone being located between the first bone and the third bone, and looping the flexible tether passed through the second tethering head in a third groove extending around the periphery of the third tethering head.

Wherein the aperture includes two separated passageways and wherein said passing includes lacing the tether loop within one passageway and around a portion of the second tethering head.

Wherein the tether is a first tether, wherein the aperture includes two separated passageways, the extension of the first looped tether is within one passageway and around a portion of the second tethered head, and which further comprises attaching a third tethering head to a third bone, the second bone being located between the first bone and the third bone; looping one end of a second flexible tether within the other passageway and around a different portion of the second tethered head, and looping the other end of the second flexible tether in a third groove extending around the periphery of the third tethering head.

Wherein the tether is a first tether, wherein the first groove is a lower groove, the first tethering head including an upper groove, and which further comprises attaching a third tethering head to a third bone, looping a second flexible tether in the upper groove extending around the periphery of the first tethering head, extending the looped second tether from the first tethering head to the third tethering head; and coupling the extension of the looped tether to the third tethering head.

Wherein the tether is an endless loop.

Which further comprises attaching together the free ends of a portion of flexible tether and creating an endless loop of tether from the portion after said passing.

Which further comprises attaching together the free ends of a portion of flexible tether and creating an endless loop of tether from the portion before said wrapping.

Which further comprises attaching together the free ends of a portion of flexible tether and creating an endless loop of tether from the portion.

Wherein said separable receiver is a first separable receiver, and which further comprises: a second separable receiver for a flexible connector, said second receiver having a second body including a second protrusion with a second passageway for a flexible connector and including a third central aperture adapted and configured to receive therein the alignment feature; wherein the lateral aperture is a first lateral aperture and said head includes a second lateral aperture spaced apart from the first lateral aperture that permits placement therethrough of the second protrusion; wherein connection of said bone connecting member to a bone aligns said receiver and said head and captures said first separable receiver and said second separable receiver within the central pocket.

Wherein said first lateral aperture is angularly spaced apart from said second lateral aperture by about ninety degrees or less; or said first lateral aperture is angularly spaced apart from said second lateral aperture by about ninety degrees or more.

Wherein said central pocket has an internal shape, the body of said separable receiver has an external shape, and the external shape is a close fit within the internal shape.

Wherein said alignment feature has an external shape, the first central aperture has an internal shape, and the external shape is a close fit within the internal shape.

Wherein said alignment feature has an external shape, the second central aperture has an internal shape, and the external shape is a close fit within the internal shape.

Wherein said head includes a bone contacting side that includes a plurality of projections adapted and configured to penetration into the bone.

Wherein said bone connecting member includes a head that covers the central pocket or the top surface.

Wherein said bone connecting member includes a threaded shaft having a lumen therethrough.

Wherein the first lateral aperture and second lateral aperture are spaced apart.

Wherein said connecting member is a threaded fastener adapted and configured for connection to a bone.

Wherein said connecting member is a first connecting member and one of said first connecting member or said head is adapted and configured for connection to a bone connecting member.

Wherein the threaded member is a set screw.

Wherein the threaded member has a top surface, said head has a top surface and when fully engaged in the slot the top surface of said threaded member is at or below the top surface of said head.

Wherein said bone connecting member includes a plate, a threaded shaft; or an anchoring head.

Wherein said bone connecting member includes a threaded shaft and said tethering head includes an aperture extending from the top surface of said tethering head through the bone contacting surface, the aperture being sized to accept therethrough the shaft.

Wherein said bone connecting member includes an anchoring head and said tethering head includes a contacting surface, and connection of said bone connecting member to the bone places the anchoring head in compression against the contacting surface.

Wherein said head has a smooth outer surface and a projection extending from the outer surface, and said passageway extends at least partly through the projection.

Wherein said cover and said bone connecting member are integral.

Wherein the entrance and exit are located proximate to each other such that the flexible tether loops around a portion of said tethering head.

Wherein said tethering head includes a bone contacting surface, the bone contacting surface being in contact with the bone when said bone connecting member is connected to a bone, said passageway being between the bone contacting surface and said cover.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A connector for coupling at least one of a first flexible tether and a second flexible tether to a bone, the connector comprising:
    a bone connecting member extending along a longitudinal axis, the bone connecting member adapted and configured for connection with the bone;
    a tethering head attached to said bone connecting member, said tethering head including first top surface extending across said tethering head, said tethering head including a through passageway extending through said tethering head, said through passageway being adapted and configured to accept therein the first flexible tether, said through passageway having an entrance, said through passageway having an exit, said through passageway having a generally V-cross-sectionally-shaped portion, said tethering head including a slot extending across said first top surface of said tethering head through said entrance of said through passageway and through said exit of said through passageway, said slot being adapted and configured and extending from said generally V-cross-sectionally-shaped portion of said through passageway to provide the first flexible tether with through access to said generally V-cross-sectionally-shaped portion of said through passageway, said tethering head having internal threads;
    a threaded member adapted and configured to be threadably received within the internal threads; and
    wherein said slot, at said entrance or exit, defines a first maximum width in a first direction substantially perpendicular to the longitudinal axis,
    said generally V-cross sectionally shaped portion, at said entrance or exit, defines a second maximum width in a second direction substantially perpendicular to the longitudinal axis,
    said second maximum width being greater than said first maximum width.

2. The connector of claim 1, wherein said generally V-cross-sectionally-shaped portion of said through passageway includes a first passageway portion extending through said tethering head and further includes a second passageway portion extending through said tethering head, wherein said first passageway portion is adapted and configured to accept therein the first flexible tether, and wherein said second passageway portion is adapted and configured to accept therein the second flexible tether.

3. The connector of claim 2, wherein said tethering head includes a ridge separating said first passageway portion and said second passageway portion.

4. The connector of claim 3, wherein said generally V-cross-sectionally-shaped portion of said through passageway includes an apex portion, and wherein said apex portion aligns with said slot.

5. The connector of claim 2, wherein said first passageway portion and second passageway portion are parallel.

6. The connector of claim 5, wherein said tethering head includes a ridge separating said first passageway portion and said second passageway portion.

7. The connector of claim 6, wherein said generally V-cross-sectionally-shaped portion of said through passageway includes an apex portion, and wherein said apex portion aligns with said slot.

8. The connector of claim 1, wherein the said threaded member is a set screw.

9. The connector of claim 1, wherein said threaded member includes a second top surface, and wherein said tethering head and said threaded member are adapted and configured to cooperate to allow said second top surface to be positioned at least one of at and below said first top surface when said threaded member is threadably received within said internal threads.

10. The connector of claim 1, wherein said tethering head has a substantially flat side adapted and configured for resting on the bone when said bone connecting member is fully inserted into the bone.

11. The connector of claim 1, wherein said threads have an outer diameter, and wherein said tethering head has a maximum width greater than said outer diameter of said threads.

12. The connector of claim 1, wherein said tethering head and said threaded member are adapted and configured to cooperate to block said through access to said generally V-cross-sectionally-shaped portion of said through passageway when said threaded member is threadably received within said internal threads.

13. The connector of claim 1, wherein said internal threads are within said through passageway.

* * * * *

UNITED STATES PATENT AND TRADEMARK OFFICE
CERTIFICATE OF CORRECTION

| | | |
|---|---|---|
| PATENT NO. | : 11,185,353 B2 | Page 1 of 1 |
| APPLICATION NO. | : 16/361967 | |
| DATED | : November 30, 2021 | |
| INVENTOR(S) | : Matthew Prygoski and Evangelos Tozakoglou | |

It is certified that error appears in the above-identified patent and that said Letters Patent is hereby corrected as shown below:

On the Title Page

Please correct the name of the Applicant in item (71) by deleting "OrthorPediatrics" and inserting in lieu thereof --OrthoPediatrics--.

Signed and Sealed this
Sixth Day of September, 2022

Katherine Kelly Vidal
*Director of the United States Patent and Trademark Office*